(12) United States Patent
Takashima et al.

(10) Patent No.: US 6,773,861 B2
(45) Date of Patent: Aug. 10, 2004

(54) UV ABSORBENT AND PREPARATION METHOD THEREOF, COMPOSITIONS AND IMAGE FORMING METHOD

(75) Inventors: Masanobu Takashima, Shizuoka-ken (JP); Hideaki Itou, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 189 days.

(21) Appl. No.: 10/156,140

(22) Filed: May 29, 2002

(65) Prior Publication Data

US 2003/0082464 A1 May 1, 2003

(30) Foreign Application Priority Data

May 30, 2001 (JP) ........................ 2001-162657

(51) Int. Cl.[7] ............................................. G03F 7/038
(52) U.S. Cl. .................... 430/270.1; 430/330; 430/329; 544/215
(58) Field of Search .............................. 430/270.1, 330, 430/329; 544/215, 216

(56) References Cited

U.S. PATENT DOCUMENTS

| 5,597,854 | A | * | 1/1997 | Birbaum et al. | ............. | 524/100 |
| 6,191,199 | B1 | * | 2/2001 | Renz et al. | ................. | 524/100 |
| 6,284,821 | B1 | * | 9/2001 | Huglin et al. | ................ | 524/100 |

FOREIGN PATENT DOCUMENTS

| DE | 19536376 A1 | * | 5/1996 | ............ G03C/1/04 |
| DE | 19750906 A1 | * | 5/1998 | ............ A61K/7/00 |
| EP | 531258 A1 | * | 3/1993 | ......... C07D/251/24 |
| EP | 706083 A1 | * | 4/1996 | ......... C07D/251/14 |
| EP | 711804 A2 | * | 5/1996 | ......... C07D/234/02 |
| JP | 08-225679 | | 9/1996 | |
| JP | 09-025360 | | 1/1997 | |
| JP | 09025360 A | * | 1/1997 | ......... C08K/5/3492 |
| JP | 11071355 A | * | 3/1999 | ......... C07D/251/24 |
| JP | 2000273437 A | * | 10/2000 | ............ C09K/3/00 |

OTHER PUBLICATIONS

806 Research Disclosure. Disclosed by Dr. Pascal Hayoz, Ciba Specialty Chemicals. Basel Switzerland. 433007. May 2000.

* cited by examiner

Primary Examiner—Mark F. Huff
Assistant Examiner—Amanda Walke

(74) Attorney, Agent, or Firm—Sughrue Mion, PLLC

(57) ABSTRACT

A UV absorbent represented by the following formula (1) [$R^1$ represents an alkenyl group, all of $R^1$ represent the same group, and $R^2$, $R^3$ and $R^4$ independently represent a hydrogen atom, an alkyl group, an alkoxy group, or a halogen atom], a method of preparing the UV absorbent due to a reaction of a compound represented by the following formula (2) and an alkenylating agent represented by the following formula (3) in the presence of a base [$R^2$, $R^3$ and $R^4$ independently represent a hydrogen atom, an alkyl group, an alkoxy group, or a halogen atom, and X represents a halogen atom, $-OSO_2R^5$ or $-OSO_2OR^1$, and $R^5$ represents an alkyl group or an aryl group], a composition containing therein the UV absorbent, and an image forming method using the composition:

Formula (1):

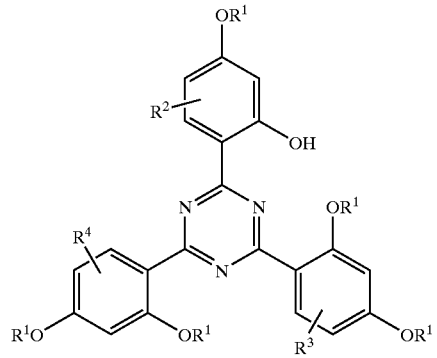

Formula (2):

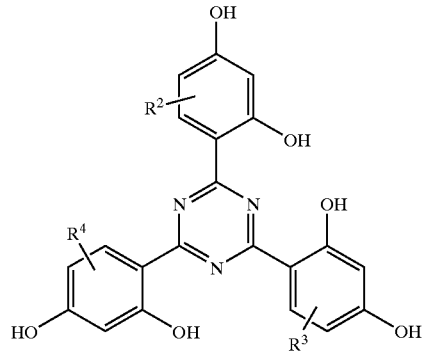

Formula (3):

$R^1-X$

20 Claims, No Drawings

UV ABSORBENT AND PREPARATION METHOD THEREOF, COMPOSITIONS AND IMAGE FORMING METHOD

BACKGROUND OF THE INVENTION

1. Field of the Invention

The present invention relates to a composition which is constantly unsusceptible to damages due to light, heat and/or oxygen, or to a composition which is useful for preparing color filters used for an LCD (liquid crystal display) and the like, and to an image forming method. More particularly, the present invention relates to a novel UV absorbent and a preparation method of the UV absorbent, and a composition containing therein the UV absorbent and an image forming method using the composition.

2. Description of the Related Art

Ordinarily, color filters to be used in a full-color LCD comprise pattern pixels having shieldability among red (R), green (G), and blue (B) pixels, respectively, in order to prevent light leakage and increase image contrast. The pattern pixels having the shieldability are formed by using a material in which a black colorant or the like is dispersed in a metallic film such as chromium or a photosensitive resin. However, in the case of the metallic film such as chromium or the like, pattern pixels are formed such that a metallic film is formed so as to cover the entire surface of a glass substrate by means of a deposition. Resist is coated on the substrate to pattern the substrate. Then, the metallic film is etched. Accordingly, processes with this method become very complicated, a yield is deteriorated thereby causing a problem with a manufacturing cost.

In order to solve the above-described problem, a method has been known in which a photosensitive black resin that is a combination of a photosensitive resin and a carbon or the like is used to form the pattern pixels having shieldability. With this method, a film thickness must have several μm in order to have the film exhibit shieldability to a certain degree. However, ordinarily, when color filters are produced, due to problems of alignment errors, pattern pixels having shieldability and R, G, and B pixels must overlap to a certain extent, and it is thus unavoidable that irregularities are produced on a surface of a color filter. Therefore, in the present situation, in order to secure a surface whose smoothness is excellent, a smoothing layer is further formed on the surface, or a surface grinding is applied to the surface.

As a method of increasing smoothness of a color filter surface, Japanese Patent Application Laid-Open (JP-A) Nos. 3-209203 and 4-69602 disclose a so-called self-alignment method. In the self-alignment method, after the formation of R, G, and B pixels, a black photosensitive resin layer is applied onto the entire surface of a substrate, the substrate is exposed to light from the rear surface thereof, the R, G and B pixels themselves are used as exposure masks, whereby pattern pixels having shieldability are formed at gaps among the pixels. However, in each of R, G, and B colorants to be generally used, transmittance of each colorant in a UV region in which a black photosensitive resin composition is cured is high. Therefore, a problem has been caused in that the UV light transmits to a photosensitive resin composition provided on the R, G and B pixels, whereby even the photosensitive resin composition is partially cured and left on a portion of the pixels.

In order to solve the problem, JP-A Nos. 62-254103, 62-9301, 1-145626, and 2-77014 each discloses a method of adding or immersing a UV light absorbent in a composition. Further, JP-A No. 9-25360 discloses a method in which a UV absorbent precursor is used in view of preventing the occurrence of exposure energy deterioration or insufficient exposure that does not reach a film deep portion which is caused by the addition of the UV absorbent or the like. Namely, with the use of the UV absorbent precursor, image-wisely irradiated exposure energy is not blocked by the UV absorbent before the energy is transmitted to the film deep portion, whereby damages caused to R, G, and B pixel portions can be prevented.

If the photosensitive resin composition contains therein the UV absorbent precursor, generally, such a compound as disclosed in JP-A No. 9-25360 which has a triazine skeleton structure and which is symmetrically structured has been used as the UV absorbent precursor. However, the compound easily produces crystalline over time especially in an atmosphere of high temperature. For this reason, during the storage of the UV absorbent precursor, the compound may produce crystallization in the photosensitive resin composition thereby causing a defect of color unevenness to a finish product such as a color filter that has been formed by using the photosensitive resin composition. As a result, there has been caused a problem in that high quality product cannot be manufactured constantly.

JP-A No. 8-225679 also discloses the UV absorbent precursor having the tiazine skeleton structure. However, not a few problems have been caused in that insufficient solubility is often seen in exemplified compounds thereof, and if solubility is imparted to a precursor compound, more reaction time is needed for the preparation of the compound.

As described above, when the UV absorbent precursor whose absorptance of exposure energy is small is used, a composition using a triazine type UV absorbent precursor, which does not easily produce crystallization even in an atmosphere of high temperature, is not yet actually provided. Further, compositions using the UV absorbent precursors which are added for constantly preventing damage due to light, heat, and/or oxygen are desired not to easily produce crystallization.

In order to prepare the UV absorbent precursor, the UV absorbent that is to be a raw material for the precursor must be prepared in advance. Namely, in order to prepare the UV absorbent precursor, another process is required, thus making it possible to increase the manufacturing cost of the UV absorbent precursor.

Research Disclosure 433007 discloses a triazine type UV absorbent which has one OH group and in which the remaining five OH groups are entirely substituted. In the description of Research Disclosure 433007, a description has been made in which the remaining five OH groups may be substituted by an alkenyl group having 2 to 50 carbon atoms. However, neither a description has been made in which the alkenyl group is particularly preferable as a substituent nor a description has been made in which the remaining five OH groups are preferable to be substituted by the same alkenyl group. Therefore, the Research Disclosure 433007 is not directed to the characteristics of the alkenyl group and does not take a preparation method of such a UV absorbent into consideration.

SUMMARY OF THE INVENTION

In order to solve the above-described various conventional problems, the objects described below will be accomplished:

A first aspect of the present invention is to provide an improved UV absorbent which can be used as the UV absorbent precursor, whose maximum absorption is within a range of short wave, which has an alkenyl ether group as a protective group which can be de-protective when heated, and which has low crystallizability.

A second aspect of the present invention is to provide a method in which a UV absorbent is manufactured inexpensively during less processes.

A third aspect of the present invention is to provide a composition containing therein a UV absorbent which does not cause any image defect due to crystallization of the UV absorbent even in an atmosphere of high temperature and which is also excellent in storage stability.

A fourth aspect of the present invention is to provide an image forming method capable of forming images due to heat and constantly forming images without defects such as color unevenness and the like by using a recording material containing therein a UV absorbent.

Means for solving the above-described problems are described below:

A first aspect of the present invention is a UV absorbent represented by the following formula (1):

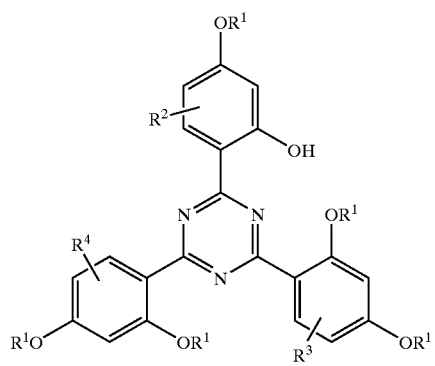

wherein $R^1$ represents an alkenyl group, each $R^1$ represents the same group, and $R^2$, $R^3$ and $R^4$ independently represent a hydrogen atom, an alkyl group, an alkoxy group, or a halogen atom.

A second aspect of the present invention is an image forming method comprising the steps of:

a) preparing a composition containing therein a UV absorbent represented by the following formula (1):

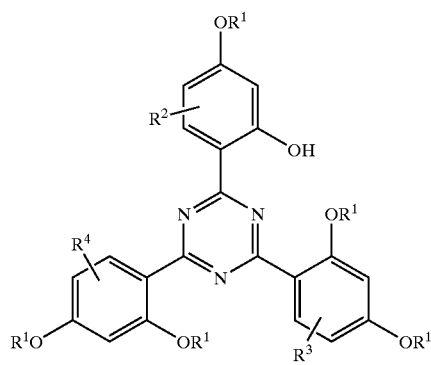

wherein, in formula (1), $R^1$ represents an alkenyl group, each $R^1$ represents the same group, and $R^2$, $R^1$ and $R^4$ independently represent a hydrogen atom, an alkyl group, an alkoxy group, or a halogen atom;

b) applying the composition onto a substrate;

c) exposing the composition on the substrate; removing unnecessary portions of the compositions by development and forming pixels on the substrate; and d) heating the pixels.

A third aspect of the present invention of a method of preparing a UV absorbent represented by the following formula (1) is produced by a reaction between a compound represented by the following formula (2) and an alkenylating agent represented by the following formula (3) in the presence of a base:

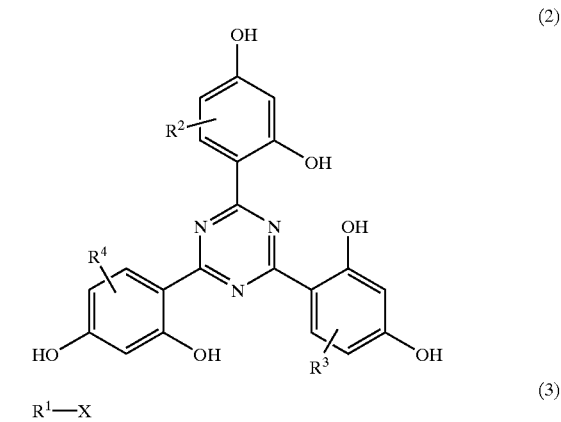

wherein, in formula (1), $R^1$ represents an alkenyl group, each $R^1$ represents the same group, $R^2$, $R^3$ and $R^4$ independently represent a hydrogen atom, an alkyl group, an alkoxy group, or a halogen atom; in formula (2), $R^2$, $R^3$ and $R^4$ independently represent a hydrogen atom, an alkyl group, an alkoxy group, or a halogen atom; and in formula (3), X represents a halogen atom, $-OSO_2R^5$, or $-OSO_2OR^1$, and $R^5$ represents an alkyl group or an aryl group.

DESCRIPTION OF THE PREFERRED EMBODIMENTS

A UV absorbent according to the present invention is characterized in that the UV absorbent has a triazine skeleton whose structure has a specified substituent. A composition of the present invention is characterized in that the composition contains therein the UV absorbent according to the present invention. Further, an image forming method of the present invention is characterized in that image recording is carried out by using a material that contains therein the composition of the present invention. Further, a method of preparing the UV absorbent of the present invention is characterized in that a specified compound and an alkenylating agent having a specified structure are reacted to each other in the presence of a base.

The UV absorbent of the present invention will be explained hereinafter in more detail. By the description, details of the method of preparing the UV absorbent, the composition containing therein the UV absorbent, and the image forming method will also be specified.

UV Absorbent The UV absorbent of the present invention is a compound represented by the following formula (1) and having a triazine skeleton structure.

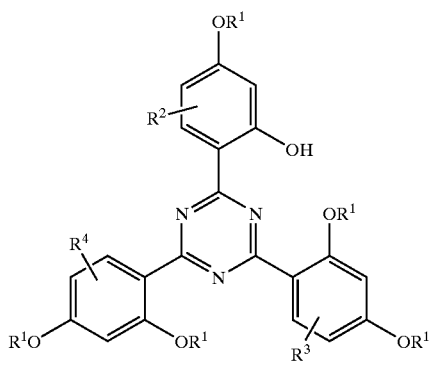

In formula (1), R¹ represents an alkenyl group, all of R¹ represent the same group. R², R³ and R⁴ independently represent a hydrogen atom, an alkyl group, an alkoxy group, or a halogen atom.

The alkenyl group represented by R¹ can be straight-chained, branched or cyclic-shaped. The number of the carbon atoms incorporated in the alkenyl group is preferably 3 to 30, more preferably 3 to 25, and particularly preferably 3 to 18. The number of carbon atoms incorporated in the alkenyl portion of the substituted alkenyl group is the same as in the case of the alkenyl group. The alkenyl group can be either substituted or unsubstituted.

Examples of substituents of the substituted alkenyl group include: halogen atoms (such as a fluorine atom, a chlorine atom or a bromine atom), a hydroxy group, alkoxy groups having 30 carbon atoms or less (such as a methoxy group, an ethoxy group, a benzyloxy group, a phenoxyethoxy group, a phenethyloxy group or the like), alkyl groups having 30 carbon atoms or less, acyl groups having 30 carbon atoms or less (such as an acetyl group, a propionyl group, a benzoyl group or the like), and aryl groups having 30 carbon atoms or less (such as a phenyl group, a 4-chlorophenyl group, a 4-methylphenyl group, or an a-naphthyl group). Here, the carboxyl group and the hydroxyl group may be in the state of a salt. During this process, examples of cations for forming the salt include organic cationic compounds, metal cations, and the like.

In the formula (1), as R¹, groups [(1) to (12)] represented by

In the formula (1), as R¹, groups [(1) to (12)] represented by constitutional formulae listed below are preferable, and among them, groups represented by (1), (2), (3), (9) and (10) are more preferable.

$$CH_2CH=CH_2 \quad (1)$$

$$CH_2CH=CHCH_3 \quad (2)$$

$$CH_2CH=CHC_2H_5 \quad (3)$$

$$CH_2CH=CHC_3H_7 \quad (4)$$

$$CH_2CH=CHC_4H_9 \quad (5)$$

$$CH_2CH=CHC_5H_{11} \quad (6)$$

$$CH_2CH=CHC_6H_{13} \quad (7)$$

$$CH_2CH=CHC_7H_{15} \quad (8)$$

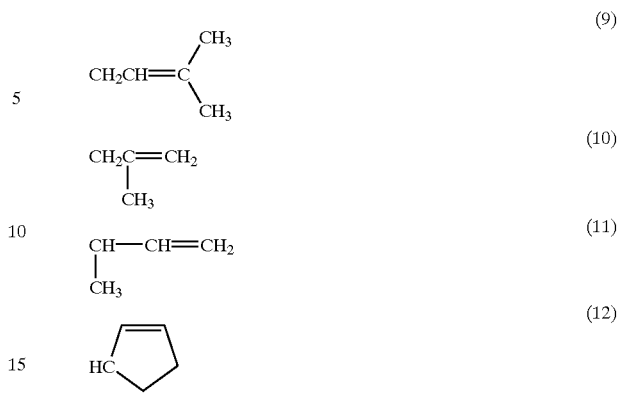

In the formula (1), R², R³ and R⁴ independently represent a hydrogen atom, an alkyl group, an alkoxy group, or a halogen atom.

The alkyl group represented by the R², R³ and R⁴ may be straight-chained, branched, or cyclic-shaped and can be unsubstituted or substituted. Examples of substituents of substituted alkyl groups that have substituents include: a carboxyl group, a sulfo group, a cyano group, halogen atoms (such as a fluorine atom, a chlorine atom or a bromine atom), a hydroxy group, alkoxycarbonyl groups having 30 carbon atoms or less (such as a methoxycarbonyl group, an ethoxycarbocyl group, or a benzyloxycarbonyl group), alkyl sulfonylaminocarbonyl groups having 30 carbons or less, an aryl sulfonylaminocarbonyl group, an alkylsulfonyl group, an arylsulfonyl group, acylaminosulfonyl groups having 30 carbon atoms or less, an alkoxy group having 30 carbon atoms or less (such as a methoxy group, an ethoxy group, a benzyloxy group, a phenoxyethoxy group, and a phenethyloxy group), alkylthio groups having 30 carbon atoms or less (such as a methylthio group, an ethylthio group, a dodecylthio group and the like), aryloxy groups having 30 carbon atoms or less (such as a phenoxy group, a p-tolyloxy group, a 1-naphthoxy group, or a 2-naphthoxy group), a nitro group, alkyl groups having 30 carbon atoms or less, an arylthio group, an alkoxycarbonyloxy group, an aryloxycarbonyloxy group, acyloxy groups having 30 carbon atoms (such as an acetyloxy group, a propionyloxy group or the like), acyl groups having 30 carbon atoms or less (such as an acetyl group, a propionyl group, a benzoyl group or the like), carbamoyl groups (such as a carbamoyl group, an N,N-dimethylcarbamoyl group, a morpholinocarbonyl group, a piperidinocarbonyl group and the like), sulphamoyl groups (such as a sulphamoyl group, an N,N-dimethylsulphamoyl group, a morphorinocarbonyl group, a piperidinosulfonyl group, an N,N-dimethylsulfomoyl group, a morpholinosulfonyl group, a piperidinosulfonyl group, and the like), aryl groups having 30 carbon atoms or less (such as a phenyl group, a 4-chlorophenyl group, a 4-methylphenyl group, an α-naphtyl group and the like), substituted amino groups (such as an amino group, an alkylamino group, a dialkylamino group, an arylamino group, a diarylamino group, an acylamino group, and the like), a substituted uleido group, a substituted phosphono group, and a heterocyclic group. Here, the carboxyl group, the sulfo group, the hydroxy group, or the phosphono group can be in the state of a salt. In that case, examples of cations for forming salts include: an organic cationic compound, a metallic cation, and the like.

Among the above-described alkyl groups, an alkyl group having 1 to 30 carbon atoms is preferable, and an alkyl group having 2 to 18 carbon atoms is more preferable, and examples of alkyl groups include: a methyl group, an ethyl group, a propyl group, an isopropyl group, a butyl group, a pentyl group, a hexyl group, an octyl group, a stearyl group, a cyclobutyl group, a cyclopentyl group, a cyclohexyl group, a t-butyl group, a t-octyl group, and the like.

The alkoxy groups represented by the above-described $R^2$ to $R^4$ can be straight-chained, branched or cyclic-shaped. Examples of substituents of substituted alkoxy groups can include the substituents similar to those of the above-described substituted alkyl group. Among the above-described alkoxy groups (excluding the above-described substituents), the alkoxy groups having 1 to 18 carbon atoms are preferable and those having 1 to 12 carbon atoms are more preferable, and examples of these alkoxy groups include: a methoxy group, an ethoxy group, a propyloxy group, a butyloxy group, a hexyloxy group, an octyloxy group, a stearyloxy group or the like.

The alkoxy groups can be substituted, and examples of subsituents thereof can include substituents similar to those of the substituted alkyl groups. Among the examples, a hydroxy group, an alkoxy group, and an alkoxy carbonyl group are preferable.

Examples of the halogen atoms represented by the above-described $R^2$ to $R^4$ can include a fluorine atom, a chlorine atom or a bromine atom, and among these halogen atoms, the chlorine atom is preferable.

As the $R^2$ to $R^4$, a hydrogen atom is particularly preferable.

Among the UV absorbents in formula (1), in view of production suitability and readiness for being de-protective by heating, a compound represented by formula (4) described below is particularly preferable:

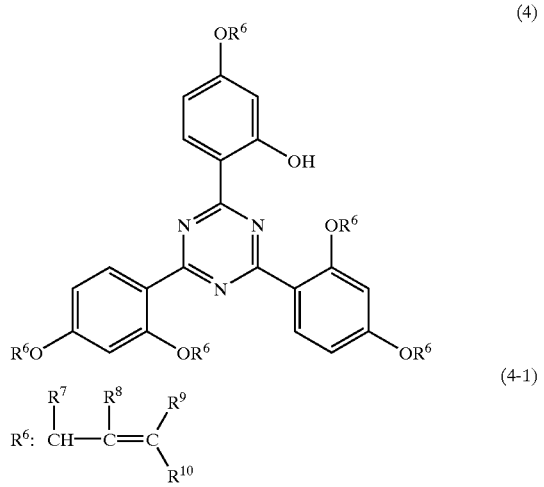

(4)

(4-1)

In formula (4), $R^6$ represents formula (4-1). In formula (4-1), $R^7$ to $R^{10}$ respectively represent a hydrogen atom or an alkyl group.

In formula (4-1), as $R^7$ to $R^{10}$, a hydrogen atom or an alkyl group having 1 to 8 carbon atoms is preferable.

The alkyl group can be straight-chained, branched or cyclic-shaped, and it is more preferable that the alkyl group is straight-chained. Further, the alkyl group can be unsubstituted or substituted.

Examples of substituents of the aforementioned alkyl group include: halogen atoms (such as a fluorine atom, a chlorine atom, and a bromine atom), a hydroxy group, alkoxy groups having 30 carbon atoms or less (such as a methoxy group, an ethoxy group, a benzyloxy group, a phenoxyethoxy group, and a phenetyloxy group), acyl groups having 30 carbon atoms or less (such as an acetyl group, a propionyl group, and a benzoyl group, aryl groups having 30 carbon atoms or less (such as a phenyl group, a 4-chlorophenyl group, a 4-methylphenyl group, and an α-naphthyl group). Here, the hydroxy group can be in the state of a salt. In that case, examples of cations for forming salts include an organic cationic compound, a metal cation, and the like.

The alkenyl group represented by formula (4-1) can be double-bonded in a cis-form or a trans-form. The double bonding can be one of the cis-form and the trans-form and a mixture thereof.

The UV absorbent of the present invention represented by formulae (1) and (4) comprises one OH group, and the other OH groups that are substituted by the same alkenyl ether groups.

The UV absorbent of the present invention can easily be synthesized by a preparation method later described. Further, when the UV absorbent is prepared, it has advantages of reducing the number of preparation processes thus lowering the preparation cost as well as making it possible to provide a stable composition without the UV absorbent being crystallized when it is added to the composition.

Furthermore, although the UV absorbent of the present invention has a maximum absorption within a range of short wave, an alkenylether group causes a Claisen re-arrangement by heating, and a hydroxy group which can conduct an intramolecular hydrogen bonding with a triazine circle appears this time, whereby the maximum absorption wavelength shifts to the side of a long wave. Therefore, the UV absorbent of the present invention can function as a photo-mask in a self-alignment system.

Method of Preparing UV Absorbent

The UV absorbent represented by formula (1) is prepared when a compound represented by formula (2) and an alkenylating agent represented by formula (3) are reacted to each other in the presence of a base.

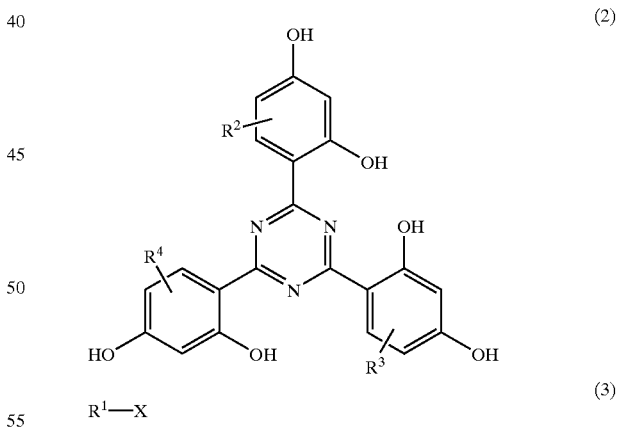

(2)

$R^1$—X  (3)

In formula (2), $R^2$, $R^3$ and $R^4$ independently represent a hydrogen atom, an alkyl group, an alkoxy group, or a halogen atom.

In formula (3), X represents a halogen atom, —$OSO_2R^5$, or —$OSO_2OR^1$. $R^5$ represents an alkyl group or an aryl group.

$R^2$ to $R^4$ in formula (2) can be explained in the same manner as that explained in formula (1).

$R^1$ of formula (3) can be explained in the same manner as that described in formula (1). Namely, $R^1$ of formula (3) represents an alkenyl group.

$R^5$ of formula (3) represents an alkyl group or an aryl group.

A description of the alkenyl group will be made in the same manner as that described in $R^2$ to $R^4$.

The aryl group can be a monocyclic or condensed ring, and may be either a substituted or unsubstituted aryl group. Examples of substituents of the substituted aryl groups include the same substituents as those of the substituted alkyl group. Among them, a substituted or unsubstituted phenyl group, a 1-naphthyl group, and a 2-naphthyl group are preferable.

An alkenylating agent represented by formula (3) used for one mole of the compound represented by formula (2) is preferably 5 moles or more, and more preferably 5.5 moles or more.

The inventors of the present invention arrived upon that an alkenylating agent successively reacts with OH groups, and and the reaction proceeds until five OH groups of the compound of formula (1) are etherified, but even if the reaction is continued, etherification of the sixth OH group hardly proceeds and the reaction of the sixth OH group is very slow.

In this way, in order to prepare the UV absorbent of formula (1), the alkenylating agent represented by formula (3) can be used in an amount of 5 moles or more with respect to the compound represented by formula (2) in an amount of 1 mole. Even if the alkenylating agent is used in an excessive amount, since etherification of the sixth OH group hardly proceeds. Therefore, the method of preparing the UV absorbent can be extremely simplified.

In the alkenylating agent represented by formula (3), X is preferably a halogen atom. Specifically, it is particularly preferably that $R^1$ is a group represented by formula (4-1) ($R^6$ in formula (4)).

Preferable examples of the alkenylating agent represented by formula (3) are listed below. However, the present invention is not limited to this.

$BrCH_2CH=CH_2$, $ClCH_2CH=CHCH_3$,
$BrCH_2CH=CHCH_3$,
$ClCH_2CH=CHC_2H_5$, $ClCH_2CH=CHC_4H_9$,
$ClCH_2CH=CHC_7H_{15}$,

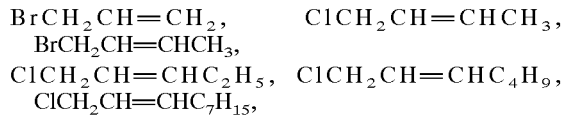

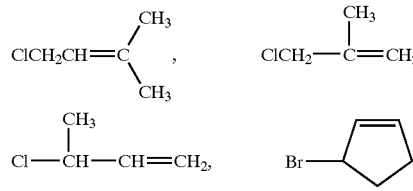

An alkenyl etherification reaction between the compound represented by formula (2) and the compound represented by formula (3) is conducted in the presence of a base.

The base can use an inorganic base or an organic base. The base is used in an amount enough for neutralizing an acid generated during the reaction between the compound of formula (2) and the alkenylated agent represented by formula (3).

Specifically, the base is used in a mole that is equal to or greater than that of the alkenylating agent to be used.

Preferably, specific examples of the base include: inorganic bases such as sodium carbonate, potassium carbonate, sodium hydrogen carbonate, calcium carbonate, magnesium oxide, cesium carbonate, and sodium acetate; or organic bases such as triethylamine, pyridine, tetramethylammoniumhydroxide, choline, and the like.

The reaction can be conducted with/without a solvent. If the solvent is not used, the alkenylating agent can be used in an excessive amount, and if the solvent is used, an organic solvent or water can be used.

It is possible to use the organic solvents which do not react with the alkenylating agent or which do not easily react therewith, and preferable examples of the organic solvents include: a hydrocarbon type solvent (such as toluene or xylene), an alcohol type solvent (such as methanole, ethanole, isopropanol or ethyleneglycol), an ether type solvent (such as tetrahydrofuran or diisopropylether), a ketone type solvent (such as acetone or cyclohexane), an amide type solvent (such as dimethylformamide, dimethylacetoamide or N-methylpyrolidone), a nitrile type solvent (such as acetonitrile), an S-containing type solvent (such as sulfolan or dioxane), an ester type solvent (such as ethyl acetate) or a halogenated hydrocarbon type solvent (such as dichlorobenzene).

As the solvent, water can be used. When water is used, the organic solvent can be mixed with water and used, and the compound of formula (2) and the compound of formula (3) can be reacted to each other in the presence of correlating transfer catalyst.

Temperature at which the compound of formula (2) and the compound of formula (3) react to each other is preferably from room temperature to 150° C., and more preferably can be chosen between 50° C. and 120° C. Further, the reaction can be conducted under a pressurizing condition.

After the completion of the reaction, the product is added into water, and isolated by being crystallized, sampled by the organic solvent, or condensed. Further, if necessary, purification such as recrystallization may be conducted. The obtained absorbent can be supplied and used in the form of fine particles or oil, or in the state of being dissolved in the organic solvents.

Specific Examples of UV Absorbent

Examples of the UV absorbent precursors represented by formula (1) are listed below. However, the present invention is not limited to these:

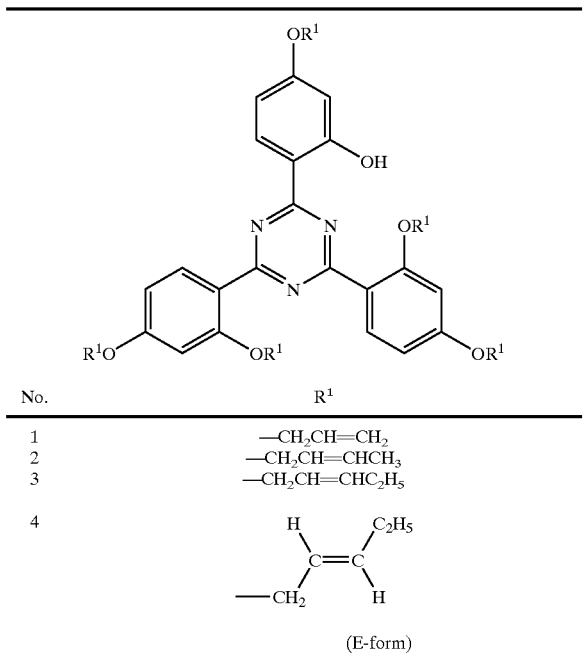

| No. | $R^1$ |
|---|---|
| 1 | $-CH_2CH=CH_2$ |
| 2 | $-CH_2CH=CHCH_3$ |
| 3 | $-CH_2CH=CHC_2H_5$ |
| 4 | (E-form) |

-continued

| No. | $R^1$ |
|---|---|
| 5 | $\begin{array}{c}H\phantom{xxx}H\\ \diagdown C=C\diagup\\ -CH_2\phantom{xx}C_2H_5\end{array}$ (Z-form) |
| 6 | $-CH_2CH=CHC_3H_7$ |
| 7 | $-CH_2CH=CHC_4H_9$ |
| 8 | $-CH_2CH=CHC_7H_{15}$ |
| 9 | $-CH_2CH=C(CH_3)_2$ |
| 10 | $-CH_2\underset{\underset{CH_3}{\mid}}{C}=CH_2$ |
| 11 | $-\underset{\underset{CH_3}{\mid}}{CH}-CH=CH_2$ |
| 12 | cyclopentyl-CH2- |
| 13 | 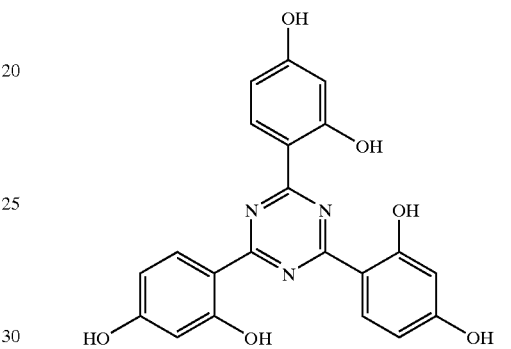 |

Examples of Preparing UV Absorbent

Examples of preparing the UV absorbent represented by formula (1) are listed below.

Further, numbers inside parentheses represent the numbers (Nos.) of the exemplified compounds that have already been described.

(1) PREPARATION EXAMPLE 1

Synthesis of an Exemplified Compound (No.1)

A compound (A) described below (40.5 g), potassium carbonate (89.7 g), allylbromide (78.7 g), dimethylacetoamide (300 ml) were measured and put in a three-necked flask, and stirred for 7 hours at an external temperature of 80° C. The reacted mixture was added to water and stirred while cooled to thereby separate crystal. The obtained crystal was filtrated and washed and rinsed with water and cooled methanol to thereby obtain a desired rough crystal.

The resultant rough crystal is recrystallized wiht acetonitrile to obtain 47.2 g of an exemplified compound No. 1 (yield 78%).

The result of analysis by $^1$H-NMR (chemical shift) is as described below, from the results, the obtained compound was confirmed to be the exemplified compound No. 1.

The result of analysis of $^1$H-NMR (($CD_3)_2$ SO): 4.66–4.87 (m, 10H), 5.27–5.50 (m, 10H), 6.00–6.18 (m, 5H), 6.58 (m, 2H), 6.75 (m, 4H), 8.29 (d, H), 8.41 (d, 1H), 13.74 (s, 1H)

Compound (A)

(2) PREPARATION EXAMPLE 2

Synthesis of an Exemplified Compound (No.1)

The compound (A) (40.5 g) and a 25% aqueous tetramethylammoniumhydroxide solution (218.4 g), and dimethylacetoamide (300 ml) were measured and put in a three-necked flask, and stirred at an internal temperature of 60° C. To the mixture was dropped allylbromide (72.6 g). After the droppage, the solution was controlled to an internal temperature of 70 to 72° C., and stirred for another 6 hours.

After the reaction, after-treatment was conducted in a manner similar to the preparation example 1 to thereby obtain the exemplified compound No. 1 (45.4 g)(75% yield).

(3) PREPARATION EXAMPLE 3

Synthesis of an Exemplified Compound (No.1)

The compound (A) (40.5 g) and a 50% aqueous cholin solution (169.4 g), and water (170 g) were measured and put in a three-necked flask, and stirred at an internal temperature of 60° C. To the mixture was dropped arylbromide (72.6 g). After the droppage, the solution was controlled to an internal temperature of 70° C. to 72° C., and stirred for another 7 hours.

After the reaction, after-treatment was conducted in a manner similar to the preparation example 1 to thereby obtain the exemplified compound No. 1 (43.6 g (72% yield)).

(4) PREPARATION EXAMPLE 4

Synthesis of an Exemplified Compound (No.2)

The compound (A) (40.5 g), potassium carbonate (82.8 g), crotylchloride (E and Z mixed body) (54.3 g), and dimethylacetoamide (300 ml) were measured and put in a three-necked flask, and stirred for 7 hours at the internal temperature of 80 to 83° C. This mixture was added to water and to this was further added ethyl acetate. This was separated, water was run off, an ethylacetate layer was dried with magnesium sulfate, magnesium sulfate was filtrated, and a solvent was removed to thereby obtain a rough product. The rough product was crystallized with a mixed solvent of acetonitrile and ethanol to thereby obtain an exemplified compound No. 2 (47.3 g) (70% yield) was obtained.

In view of the results of analysis of $^1$H-NMR, the obtained compound was confirmed to be an exemplified compound No. 2.

The results of analysis of $^1$H-NMR ((CD$_3$)$_2$ SO): 1.71 (m, 15H), 4.56–4.84 (m, 10H), 5.64–5.90 (m, 10H), 6.53 (m, 2H), 6.64 (m, 4H), 8.30 (d, 2H), 8.40 (d, 1H), 13.73 (d, 1H).

(5) PREPARATION EXAMPLE 5

Synthesis of an Exemplified Compound (No.5)

A rough product was obtained in a manner similar to the preparation example 4 except that the following compound (B) (6.27 g) was used instead of crotylchloride (54.3 g) of the Preparation Example (4). The rough product was purified by silica gel column (solvent n-hexane/ethylacetate=4/1) to thereby obtain an exemplified compound No. 5 (58.9 g) (79% yield).

In view of the results of analysis of $^1$H-NMR, the obtained compound was confirmed to be an exemplified compound No. 5.

The results of analysis of $^1$H-NMR ((CD$_3$)$_2$ SO): 1.00 (m, 15H), 2.18 (m, 10H), 4.60–4.94 (m, 10H), 5.54–5.74 (m, 10H), 6.50–6.75 (m, 6H), 8.30 (d, 2H), 8.40 (d, 1H), 13.73 (s, 1H).

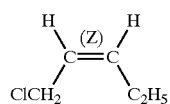

Compound (B)

(6) PREPARATION EXAMPLE 6

Synthesis of an Exemplified Compound (No.9)

A rough product was obtained in the same manner as the preparation example 4 except that 1-chloro-3-methyl-2-butyn (62.7 g) was used instead of crotylchloride (54.3 g) of the preparation example 4. The rough product was purified by silica gel column (solvent n-hexane/ethylacetate=4/1) to thereby obtain an exemplified compound No. 9 (55.9 g) (75% yield).

In view of the results of analysis of $^1$H-NMR, the obtained compound was confirmed to be an exemplified compound No. 9.

The results of analysis of $^1$H-NMR ((CD$_3$)$_2$ SO): 1.72 (s, 30H), 4.60–4.80 (m, 10H), 5.40–5.58 (m, 5H), 6.50 (m, 2H), 6.70 (m, 4H), 8.31 (d, 2H), 8.40 (d, 1H), 13.74 (s, 1H).

(7) PREPARATION EXAMPLE 7

Synthesis of an Exemplified Compound (No.10)

A rough product was obtained in the same manner as the preparation example 4 except that 3-chloro-2-methyl-1-propene (54.3 g) was used instead of crotylchloride (54.3 g) of the preparation example 4. The rough product was purified by silica gel column (solvent n-hexane/ethylacetate=4/1) to thereby obtain an exemplified compound No. 10 (47.3 g) (70% yield).

In view of the results of analysis of $^1$H-NMR, the obtained compound was confirmed to be an exemplified compound No. 10.

The results of analysis of $^1$H-NMR ((CD$_3$)$_2$ SO): 1.78 (d, 15H), 4.56 (s, 6H), 4.70 (s, 4H), 4.94–5.12 (m, 10H), 6.52 (m, 2H), 6.72 (m, 4H), 8.22 (d, 2H), 8.38 (d, 1H), 13.74 (s, 1H).

The UV absorbent of the present invention can be used as a stabilizer for organic materials to prevent damages due to light, heat and/or oxygen. Examples of the organic materials to be stabilized include: photographing materials, heat-sensitive recording materials, photosensitive/heat-sensitive recording materials, ink jet materials, plastics, coatings, rubbers, cosmetics, liquid crystal materials, color filters, and the like, and compositions containing therein the UV absorbent of the present invention can be used as the compositions for these uses. The UV absorbent of the present invention can be used for a photosensitive resin composition. The UV absorbent is used as the aforementioned stabilizer as described above. Besides, the UV absorbent can control exposure energy in the vicinity of 360 nm which is applicable to the photosensitive resin composition by utilizing a de-protective reaction of protective groups of the UV absorbent. It is particularly preferable that the photosensitive resin composition is used as a color filter.

Photosensitive Resin Composition

The composition of the present invention contains therein the UV absorbent, and, for example, may be structured by containing the UV absorbent of the present invention in a known photosensitive resin composition.

For example, all of the photosensitive resin compositions disclosed in JP-A No. 3-282404 can be used as the known photosensitive resin compositions. Specific examples of the photosensitive resin compositions disclosed in JP-A No. 3-282404 include: a photosensitive resin composition comprising a negative type diazo resin and a binder; a photopolymerizable resin composition; a photosensitive resin composition comprising an azido compound and a binder; a cinnamic acid based photosensitive resin composition, and the like. Further, a positive type photosensitive resin composition comprising a phenol resin and a quinondiazido compound can also be used.

Of the photosensitive resin compositions listed above, the photopolymerizable resin composition is particularly preferable. Namely, as the photosensitive resin composition of the present invention, it is preferable to use a photosensitive resin composition containing therein at least a binder, a polymerizable monomer, and a photopolymerization initiator other than the UV absorbent of the present invention.

Further, the photosensitive resin composition of the present invention can contain other components such as colorants and the like as necessary.

UV Absorbent

As a UV absorbent, the UV absorbent of the present invention that has already been described is used. Since UV absorptivity of the UV absorbent is relatively low before image forming, exposure energy that was exposed image-wisely with the UV absorbent is hardly absorbed by the UV absorbent, whereby the film can be sufficiently exposed to a sufficient depth thereof. Further, as described above, since the UV absorbent exhibits low crystallizability even in an atmosphere of high temperature, and does not separate, image defects due to the crystallization can be inhibited.

The content of the UV absorbent in the photosensitive resin composition of the present invention with respect to a mass of the total solid components thereof is preferably 0.1 to 30 mass %, more preferably 0.1 to 20 mass %, and particularly preferably 0.5 to 10 mass %.

The UV absorbent represented by formula (1) can be used singly or two or more thereof can be used in combination. Besides the UV absorbent represented by formula (1), the UV absorbent precursors disclosed in JP-A Nos. 9-25360 and 8-225679 can be used together.

Binder

Binders are not particularly limited, and ordinary film formable polymers can be used as binders. Of the binders, preferable are those that have appropriate pigment dispersibility, compatibility with polymerizable monomers or photopolymerization initiators, solubility with alkaline developers, solubility with organic solvents during the preparation of coating solutions, strength, and softening temperature.

Specific examples of the binders include: a methacrylic acid copolymer, an acrylic acid copolymer, an itaconic acid copolymer, a crotonic acid copolymer, a maleic acid copolymer, a partially esterified maleic acid copolymer, a copolymer of a (metha) acrylic acid and a (metha) acrylic ester, a copolymer of styrene/maleic anhydride, and reactants of these copolymers and alcohols. Those are disclosed in Japanese Patent Application Laid-Open (JP-A) Nos. 59-44615, 11-269210, 10-45816, 59-53836, and 59-71048, and Japanese Patent Application Publication (JP-B) Nos. 54-34327, 58-12577, and 54-25957. Moreover, cellulose derivatives having carboxylic acid groups at the side chains thereof can be used.

In addition to the above-description, binders in which a cyclic acid anhydride is added to a polymer having a hydroxyl group are suitably available. Particularly, a copolymer of benzil (metha) acrylate and (metha) acrylic acid or a multi-copolymer of benzil (metha) acrylate and (metha) acrylic acid and another monomer, that are disclosed in U.S. Pat. No. 4,139,391 can be used.

Of these binders, the copolymer of (metha) acrylic acid and (metha) acrylic acid ester is preferably used.

A molecular weight of the binder is preferably from 5,000 to 200,000. The binder can be used solely or in a state of a composition in combination with an ordinary film formable polymer.

Further, the content of the binder in the photosensitive resin composition with respect to a mass of the total solid components of the photosensitive resin composition is preferably 1 to 80 mass %.

Polymerizable Monomer

As a polymerizable monomer, a compound having at least one addition-polymerizable ethylenically unsaturated group can be listed.

Specific examples of the polymerizable monomers include: monofunctional acrylates or monofunctional methacrylates such as polyethylene glycol mono(metha)acrylate, polypropylene glycol mono(metha)acrylate and phenoxyethyl(metha)acrylate; polyethylene glycol di(metha)acrylate, polypropylene glycol di(metha)acrylate, trimethylolethanetriacrylate, trimethylolpropane triacrylate, trimethylolpropane diacrylate, neopentyl glycol di(metha) acrylate, pentaerythritol tetra(metha)acrylate, pentaerythritol tri(metha)acryalte, dipentaerythritol hexa(metha) acrylate, dipentaerythritol pentha(metha)acrylate, hexanediole di(metha)acrylate, trimethylolpropane tri (acyloiloxypropyl)ether, tri(acryloiloxyethyl)isocyanurate, tri(acryloyloxyethyl)cyanurate, and glycerin tri(metha) acrylate; and multifunctional acrylates or multifunctional (metha)acrylates such as those that were (metha)acrylated after ethyleneoxide or propyleneoxide was added to a mulifunctional alcohol such as trimethylolpropane or glycerine.

Further, specific examples of the polymerizable monomers include: multifunctional acrylates or multifunctional methacrylates such as known (metha)acrylic esters, urethane (metha)acrylates, (metha)acrylic amides, allyl compounds, and vinyl esters that are disclosed in JP-A No. 60-258539; urethane acrylates that are disclosed in JP-B Nos. 48-41708 and 50-6034 and JP-A No. 51-37193; polyester acrylates that are disclosed in JP-A No. 48-64183 and JP-B Nos. 49-43191 and 52-30490; and epoxy acrylates which are reaction products of epoxy resin and (metha)acrylic acid.

Of the polymerizable monomers, preferable are (metha) acrylic esters such as trimethylolpropane tri(metha)acrylate, pentaerythritol tetra(metha)acrylate, dipentaerythritol hexa (metha)acrylate, and dipentaerythritol pentha(metha) acrylate.

The polymerizable monomers can be used singly or two or more of them can be used in combination.

The content of the polymerizable monomer in the photopolymerizable resin composition with respect to a mass of the total solid components of the photopolymerizable resin composition is preferably 5 to 80 mass %, and more preferably 10 to 60 mass %.

Photopolymerization Initiator

Examples of photopolymerization initiators include: a vicinal polyketoldonyl compound disclosed in U.S. Pat. No. 2,367,660, an acyloin ether compound disclosed in U.S. Pat. No. 2,448,828, an aromatic acyloin compound which is substituted by α-hydrocarbon disclosed in U.S. Pat. No. 2,722,512, a polynuclear quinone compound disclosed in U.S. Pat. Nos. 3,046,127 and 2,951,758, a combination of a triarylimidazol dimer and p-aminoketone disclosed in U.S. Pat. No. 3,549,367, a benzothiazole compound and a trihalomethyl-s-triazine compound disclosed in JP-B No. 51-48516, a trihalomethyl-s-triazine compound disclosed in U.S. Pat. No. 4,239,850, and a trihalomethyloxadiazole compound disclosed in U.S. Pat. No. 4,212,976.

Further, examples of the photopolymerization initiators include: aromatic ketones such as benzophenone, camphorquinone, 4,4-bis(dimethylamino)benzophenone, 4-methoxy-4'-dimethylaminobenzophenone, 4,4'-dimethoxybenzophenone, 4-dimethylaminobenzophenone, 4-dimethylaminoacetophenone, benzil anthraquinone, 2-tert-butylanthraquinone, 2-methylanthraquinone, xanthone, thioxanthone, 2-chlorthioxanthone, 2,4-diethylthioxanthone, fluorenone, acridone, and bisacylphosphine oxides such as bis (2,4,6-trimethylbenzoyl)-phenylphosphine oxide, acylphosphine oxides such as Lucirin TPO, dialkoxyaceto phenones, α-hydroxy or α-aminoaceto phenones, and α-hydroxycycloalkylphenyl ketones, benzoin and benzoin ethers such as benzoin methyl ether, benzoin ethyl ether, benzoin isopropyl ether, and benzoin phenyl ether; 2,4,5-triarylimidazole dimers such as 2-(o-chlorophenyl)-4,5-diphenylimidazole dimer, 2-(o-chlorophenyl) -4,5-di(m-methoxyphenyl)imidazole dimer, 2-(o-fluorophenyl) -4,5-diphenylimidazole dimer, 2-(o-methoxyphenyl)-4,5-diphenylimidazole dimer, and 2-(p-methoxyphenyl)-4,5-diphenylimidazole dimer; and compounds disclosed in U.S. Pat. Nos. 3,784,557, 4,252,887, 4,311,783, 4,459,349, 4,410,621, and 4,622,286; polyhalogen compounds such as carbon tetrabromide, phenyltribromomethyl sulfone, and phenyltrichloromethyl ketone; compounds disclosed in JP-A No. 59-133428, JP-B Nos. 57-1819 and 57-6096, and U.S. Pat. No. 3,615,455; S-triazine derivatives, having trihalogen-substituted methyl groups disclosed in JP-A No. 58-29803, such as 2,4,6-tris (trichloromethyl)-S-triazine, 2-methoxy-4,6-bis (trichloromethyl)-S-triazine, 2-amino-4,6-bis (trichloromethyl)-S-triazine, and 2-(P-methoxystyryl)-4,6-bis(trichloromethyl)-S-triazine; organic peroxides disclosed in JP-A No. 59-189340 such as methylethylketone peroxide, cyclohexanone peroxide, 3,3,5-trimethylcyclohexanone peroxide, benzoyl peroxide, ditertiary-butyldiperoxyisophthalate, 2,5-dimethyl-2,5-di(benzoylperoxy)hexane, tertiary-butylperoxybenzoate, a,a'-bis(tertiary-butylperoxyisopropyl)benzene, dicumyl peroxide, and 3,3',4,'4-tetra-(tertiarybutylperoxycarbonyl)benzophenone; azinium salts disclosed in U.S. Pat. No. 4,743,530; organic boron compounds; phenylglyoxal acid esters such as methyl phenylglyoxalates; titanothenes such as bis($\eta^5$-2,4-cyclopentadiene-1-yl)-bis(2,6-difluoro-3-(1H-pyrrole-1-yl)-phenyl)titanium; iron-allene complex such as $\eta^5$-cyclopentadienyl-$\eta^6$-cumenyl-iron(1+)-hexafluorophosphate(1−); diaryliodonium salts such as diphenyliodonium salts; and triarylsulfonium salts such as triphenylsulfonium salts.

More detailed examples of compounds of the above-described photopolymerization initiators, and examples of photopolymerization initiators of another type are disclosed in paragraph Nos. [0067] to [0132] of JP-A No. 10-45816.

The photopolymerization initiators can use a material comprising a combination of two compounds or more. Examples of such combinations include: a combination of 2,4,5-triarylimidazol dimer and mercaptobenzoxazol or the like; a combination of 4,4'-bis(dimethylamino)benzophenone and benzophenone and benzoinmethylether disclosed in U.S. Pat. No. 3,427,161; a combination of benzoyl-N-methylnaphthothiazolin and 2,4-bis(trichloromethyl)-6-(4'-methoxyphenyl)-triazole disclosed in U.S. Pat. No. 4,239,850; a combination of dialkylaminobenzoic acid ester and dimethyltioxanthone disclosed in JP-A No. 57-23602, and a combination of three compounds i.e., 4,4-bis(dimethylamino)benzophenone, benzophenone and a polyhalogenated methyl compound disclosed in JP-A No. 59-78339.

In the case of a photopolymerization initiator comprising a combination of two compounds or more, it is preferable to use a combination of 4,4'-bis(diethylamino)benzophenone and benzophenone, a combination of 2,4-diethylthioxanthone and 4-dimethylamino ethyl benzoate, or a combination of 4,4'-bis(diethylamino)benzophenone and 2,4,5-triarylimidazole dimer.

Examples of the organic boron compounds include: organic boron compounds disclosed in JP-A Nos. 62-143044, 9-188685, 9-188686, and 9-188710, respectively, or spectral sensitized dyes obtained from cationic dyes.

Of the photopolymerization initiators, trihalomethyl-s-triazine, trihalomethyloxadiazole and triarylimidazole dimer are preferable.

The content of the photopolymerization initiator in the photosensitive resin composition with respect to a mass of the total solid components of the photosensitive resin composition is generally 0.01 to 20 mass %, and preferably 0.1 to 15 mass %.

In the UV absorbent precursor of the present invention, if a protective group is particularly $COOC_4H_9(t)$, the UV absorbent precursor and an acid generator are used together to form the photosensitive resin composition. Examples of acid generators include: a light acid generator and a thermal acid generator. Specific Examples of generators include: aromatic diazonium salts, aromatic iodonium salts, sulfonium salts, organic halogenides, sulfonic acid esters of phenol compounds, and imido sulfonates .

Other Components

The compositions and the photosensitive resin compositions of the present invention can contain other components such as colorants, solvents, thermal polymerization inhibitors, dispersion aids, plasticizers, surfactants, and adhesion accelerators.

Colorants

As the colorants, known dyes or pigments may be used. Pigments are particularly preferable in respects of light-resistance, heat-resistance, and chemical resistance.

The pigments are used by being uniformly dispersed in the composition, but the particle diameter of each of the pigments is preferably 5 $\mu$m or less, and particularly preferably 1 $\mu$m or less. Further, if the pigments are used for preparing a color filter, a particle diameter of the pigment is preferably 0.5 $\mu$m or less.

As the pigments, red, green and blue pigments are used.

Examples of the red pigments include: C.I. Pigment Red 9, C.I. Pigment Red 97, C.I. Pigment Red 122, C.I. Pigment Red 123, C.I. Pigment Red 149, C.I. Pigment Red 168, C.I. Pigment Red 177, C.I. Pigment Red 180, C.I. Pigment Red 192, C.I. Pigment Red 215, C.I. Pigment Red 216, C.I. Pigment Red 217, C.I. Pigment Red 220, C.I. Pigment Red 223, C.I. Pigment Red 224, C.I. Pigment Red 226, C.I. Pigment Red 227, C.I. Pigment Red 228, C.I. Pigment Red 240, C.I. Pigment Red 48:1, C.I. Pigment Red 242, C.I. Pigment Red 209, C.I. Pigment Red 146, C.I. Pigment Red 11, C.I. Pigment Red 81, C.I. Pigment Red 213, C.I. Pigment Red 272, C.I. Pigment Red 270, C.I. Pigment Red 255, C.I. Pigment Red 264, and C.I. Pigment Red 254.

Examples of the green pigments include: C.I. Pigment Green 7, C.I. Pigment Green 36, and the like.

Examples of the blue pigments include: C.I. Pigment Blue 15, C.I. Pigment Blue 15:6, C.I. Pigment Blue 22, C.I. Pigment Blue 60, and C.I. Pigment Blue 64.

Besides the aforementioned pigments, yellow pigments, orange pigments, violet pigments, brown pigments, and black pigments can be used as necessary.

Examples of the yellow pigments include: C.I. Pigment Yellow 20, C.I. Pigment Yellow 24, C.I. Pigment Yellow 12, C.I. Pigment Yellow 17, and C.I. Pigment Yellow 83, C.I. Pigment Yellow 86, C.I. Pigment Yellow 93, C.I. Pigment Yellow 109, C.I. Pigment Yellow 110, C.I. Pigment Yellow 117, C.I. Pigment Yellow 125, C.I. Pigment Yellow 137, C.I. Pigment Yellow 138, C.I. Pigment Yellow 139, C.I. Pigment Yellow 147, C.I. Pigment Yellow 148, C.I. Pigment Yellow 150, C.I. Pigment Yellow 153, C.I. Pigment Yellow, C.I. Pigment Yellow 154, C.I. Pigment Yellow 166, C.I. Pigment Yellow 168, and C.I. Pigment Yellow 185.

Examples of the orange pigments include: C.I. Pigment Orange 36, C.I. Pigment Orange 43, C.I. Pigment Orange 51, C.I. Pigment Orange 55, C.I. Pigment Orange 59, C.I. Pigment Orange 61, and C.I. Pigment Orange 71.

Examples of the violet pigments include: C.I. Pigment Violet 19, C.I. Pigment Violet 23, C.I. Pigment Violet 29, C.I. Pigment Violet 30, C.I. Pigment Violet 37, C.I. Pigment Violet 40, and C.I. Pigment Violet 50.

Examples of the brown pigments include: C.I. Pigment Brown 23, C.I. Pigment Brown 25, and C.I. Pigment Brown 26. Examples of the black pigment include C.I. Pigment Black 7 and the like.

The aforementioned pigments can be used singly or two or more of them can be used in combination.

Of the pigments described above, Pigment Yellow 138, Pigment Yellow 139, Pigment Yellow 185, Pigment Red 254, Pigment Green 36, and Pigment Blue 15 are preferable.

The content of the colorant in the composition with respect to a mass of the total solid components of the composition is preferably 0.1 to 70 mass %, and more preferably 1 to 50 mass %.

Solvents

As will be described later in the image forming method of the present invention, when the photosensitive resin composition is disposed on a support or the like, a coating solution in which the photosensitive resin composition containing therein various components was dissolved in a solvent is used.

Examples of the solvents to be used in this occasion include: so-called cellosolves such as ethylene glycol monomethylether, ethylene glycol monoethylether, propylene glycol monomethylether, propylene glycol monomethylether acetate, propylene glycol monoethylether, diethylene glycol monomethylether, and ethylene glycol monoethylether; and acetates such as acetate, ethyl acetate, n-propyl acetate, i-propyl acetate, n-butyl acetate, and i-butyl acetate; aromatic hydrocarbons such as benzene, toluene, and xylene; ketones such as methylethyl ketone, acetone, methylisobutyl ketone, and cyclohexanone; and alcohols such as ethanol, propanol, butanol, hexanol, cyclohexanol, ethylene glycol, diethylene glycol, and glycerine.

Thermal Polymerization Inhibitors

Examples of the thermal polymerization inhibitors include: hydroquinone, p-methoxyphenol, di-t-butyl-p-cresol, pyrogallol, t-butylcatechol, benzoquinone, 4,4'-thio bis (3-methyl-6-t-butylphenol), 2,2'-methylene bis(4-methyl-6-t-butylphenol), 2-melcaptobenzoimidazole, and phenothiazine. The thermal polymerization inhibitors can be used as long as the effects of the present invention are not lost.

The dispersion aids, plasticizers, surfactants, or adhesion accelerators can appropriately be chosen from known ones and used as long as the effects of the present invention are not damaged.

As will be described later, the photosensitive resin composition of the present invention is useful to produce color filters. Besides, the photosensitive resin composition of the present invention is suitably useful to produce recording materials for recording images by heating, such as (photosensitive or) heat sensitive recording materials in which images are recorded by heat-generating elements such as thermal heads or laser heat type heat-sensitive recording materials which are recorded due to laser-converting heat, to produce resists for manufacturing printing substrates or photomasks, and to produce black & white or color transfer-developing sheets or color-developing sheets. In accordance with the uses of the materials, other components can be added.

Image Forming Method

The image forming method of the present invention comprises at least steps of providing the above-described photosensitive resin composition of the present invention on a substrate (hereinafter, sometimes, a "photosensitive resin layer forming step"), exposing a photosensitive resin composition on the substrate (hereinafter, sometimes, an "exposure step"), removing unnecessary resin compositions to be removed by a development processing and forming pixels on the substrate (hereinafter, sometimes, a "pixels-forming step"), and conducting a heat treatment on the pixels formed on the substrate (hereinafter, sometimes, a "heat-treatment step"). The four steps may be repeated a plurality of times.

The photosensitive resin compositions each containing therein colorants having different hues are used and the four steps are repeated a plurality of times to thereby form a multi-colored image.

In the photosensitive resin layer forming step, the photosensitive resin composition that contains therein at least the UV absorbent represented by formula (1), a binder, a polymerizable monomer and a photopolymerization initiator is provided on the substrate. In this case, examples of methods for providing the photosensitive resin composition on the substrate include: (i) a method for forming a layer (hereinafter, sometimes, a "photosensitive resin layer") by preparing a coating solution in which the photosensitive resin composition was dissolved in a solvent, applying the coating solution on the substrate by a known application method, and then drying it; and (ii) a method for providing the photosensitive resin composition on the substrate by preparing a transferring material in which a photosensitive resin layer was previously applied on a temporary support by a known application method.

In the method (ii), the photosensitive resin layer is temporarily peeled off from the temporary support, and can be used as an independent sheet (photosensitive sheet).

Examples of the known application methods include those using a spinner, a whirler, a roller coater, a curtain coater, a knife coater, a wire bar coater, an extruder, and the like. The coating solution was applied, and then dried, whereby the photosensitive resin layer or a photosensitive sheet can be obtained.

The transferring material in the method (ii) according to a specific aspect can be structured in a manner similar to a known photosensitive transfer material, and the simplest aspect thereof is such that a thin layer (photosensitive resin layer) comprising the photosensitive resin composition is formed on the temporary support formed by a flexible plastic film or the like. Further, an undercoating layer, an intermediate layer, a peel-off layer, and the like, which can facilitate peelability at the interface between the support and the photosensitive resin layer and impart shock absorbability, can arbitrarily be provided between the support and the photosensitive resin layer of the transferring material.

Specific examples of the transferring materials include: a transferring material which is disclosed in JP-A No. 4-208940 and which has a photosensitive resin layer and a separating layer whose adhesiveness to a temporary support is low; a photosensitive transfer material which is disclosed in JP-A No. 5-173320, which has a thermoplastic resin layer, an intermediate layer, and a photosensitive resin layer on a temporary support and in which adhesiveness between the temporary support and the thermoplastic resin layer is the lowest; a transferring material which is disclosed in JP-A No. 5-72724, which has a thermoplastic resin layer, a separating layer, and a photosensitive resin layer and in which adhesiveness between the thermoplastic resin layer and the separating layer is the lowest; and a photosensitive transfer material which is disclosed in JP-A No. 5-80503, which has a thermoplastic resin layer, an intermediate layer, and a photosensitive resin layer on a temporary support and in which adhesiveness between the temporary support and the thermoplastic resin layer is the lowest.

Of the transferring materials, a photosensitive transfer material of an aspect that is structured by layering a thermoplastic resin layer that is alkaline-soluble, an intermediate layer, and a photosensitive resin layer on the temporary support in this order is preferable. Further, a protective film can be layered on the photosensitive resin layer as necessary.

If the photosensitive resin composition is provided on a substrate by the method (ii), the photosensitive resin composition can be provided on the substrate by removing the protective film from the transferring material as necessary, adhering the photosensitive resin layer to the substrate due to pressure and heat, and then, peeing the temporary support off from the substrate, and the like. In order to adhere the photosensitive resin layer to the substrate, known laminator and/or vacuum laminator can be used, and in order to increase the productivity, an auto-cut laminator can also be used.

In the exposure step, light is irradiated imagewisely onto the photosensitive resin composition which is provided on the substrate with/without the presence of a predetermined photomask (patterning exposure).

Examples of light sources include known light sources such as an extra-high pressure mercury lamp and a xenon lamp. The photomask can appropriately be selected from known ones.

In the pixels-forming step, unnecessary photosensitive resin compositions (unnecessary regions that are not used for forming pixels on the photosensitive resin layer) are removed by the development processing to thereby form pixels on the substrate.

As a developer used for the development processing, in a case of a negative photosensitive resin layer, a solvent or an alkaline solution, which dissolves unexposed portions and which does not dissolve exposed portions, is used. Meanwhile, in a case of a positive photosensitive resin layer, a solvent acting vice versa in the case of the negative photosensitive resin layer is used. From a recent environmental viewpoint, it is preferable for both the negative photosensitive resin layer and the positive photosensitive resin layer to conduct the development processing using the alkaline solution. For example, a diluted solution solution of an alkaline substance or a mixture of the diluted solution and a slight amount of an organic solvent that is miscible with water can be used.

Examples of the alkaline substances include: alkaline metal hydroxides (such as sodium hydroxide, potassium hydroxide, and the like), alkaline metal carbonates (such as sodium carbonate, potassium carbonate, and the like), alkaline metal bicarbonates (such as sodium bicarbonate, potassium bicarbonate, and the like), alkaline metal silicates (such as sodium silicate, potassium silicate, and the like), alkaline metal metasilicates (such as sodium metasilicate, potassium metasilicate, and the like), triethanol amine, diethanol amine, monoethanol amine, morphorine, tetraalkyl ammonium hydroxides (such as tetramethyl ammonium hydroxide), and sodium triphosphate.

Concentration of alkaline substances is preferably 0.01 to 30 mass %, and pH is preferably 8 to 14.

Examples of suitable organic solvents which are miscible with water include: methanol, ethanol, 2-propanol, 1-propanol, butanol, ethyleneglycol monomethylether, ethyleneglycol monoethylether, ethyleneglycol mono n-butylether, benzilalcohol, acetone, methylethylketone, cyclohexanone, $\epsilon$-caprolactone, $\gamma$-butyrolactone, dimethylformamide, dimethylacetoamide, hexamethyl phospholamide, ethyl lactate, methyl lactate, $\epsilon$-caprolactam, and N-methylpyrolidone. Concentration of the organic solvents which is miscible with water is preferably 0. 1 to 30 mass %.

Further, a known surfactant can be added to the developer and the concentration of the surfactant is preferably 0.01 to 10 mass %.

The developer can be used as a bath liquid or a spray liquid. When unnecessary regions are removed from the photosensitive resin layer, the unnecessary regions can be removed by rubbing with a rotating brush or a wetting sponge in the developer.

Ordinarily, the temperature of the developer is preferably the neighborhood of room temperature to 40° C. A washing processing can be provided after the development processing.

In the heat treatment step, pixels formed on the substrate are heated to further cure the pixels, the UV absorbent represented by formula (1) contained in the pixels are decomposed, and the UV absorbent is converted to the one whose maximum absorbing wavelength is a long wave.

Examples of heating methods include known heating methods using a convection oven, a hot plate, an infrared heater, and the like. A heat treatment condition is selected such that UV absorbability absorbing a long wave is sufficiently exhibited when a UV absorbent whose maximum absorbing wavelength is a short wave is connected to a UV absorbent whose maximum absorbing wavelength is a long wave. The temperature of the heat treatment is preferably 120 to 300° C., and particularly preferably 130 to 250° C. Further, heating time is preferably 1 to 200 minutes.

A ratio of a transmittance by 365 nm light of the photosensitive resin layer before the exposure to a transmittance by 365 nm light of the photosensitive resin layer after the heat treatment is preferably 1:0.99 to 1:0.00001, more preferably 1:0.5 to 1:0.00001, and most preferably 1:0.1 to 1:0.00001.

Next, as a specific example of the image forming method of the present invention, an example of preparing color filters will be explained. The color filters can be prepared by sequentially repeating four steps (from the photosensitive resin layer forming step to the heat treatment step) of the image forming method according to the present invention for each of red (R) pixels, green (G) pixels, and blue (B) pixels. For example, the color filters can be prepared by repeating steps (1) to (4) described below for R, G, and B pixels, respectively:]

(1) a step in which the photosensitive resin composition containing therein a UV absorbent represented by formula (1), a polymerizable monomer, a photopolymerization initiator, and a binder is added to a solvent to thereby form a coating solution. A coating solution (coating solution for the photosensitive resin layer) in which pigments are further dispersed in the coating solution is coated on the substrate, and dried. Otherwise, as described above, the transferring material on which the photosensitive resin layer has previously been formed on the temporary support is used, and the photosensitive layer is transferred to a substrate. Accordingly, a colored photosensitive resin layer was obtained on the substrate (photosensitive resin layer forming step);

(2) a step in which the colored photosensitive resin layer is pattern-exposed through the photomask (the exposure step);

(3) a step in which, after the exposure, the development processing of the photosensitive resin layer is conducted to thereby form pixels consisting of exposed portions of the photosensitive resin layer (the pixels-forming step); and (4) a step in which the pixels formed on the substrate are fired by the heat treatment, and further cured (the heat treatment step).

In the step (1), a pigment having a desired hue is selected, coating solutions for R, G, and B colors are prepared and used, whereby pixels for R, G, and B colors are sequentially formed on the substrate. Beginning with the second color, a layer can be formed so as to cover the first color pixels. Only the region that was not cured is dissolved and removed by the development processing.

The step (1) is preferably carried out by using a method in which the photosensitive resin composition is provided on the substrate by using the transferring material in which the photosensitive resin layer was previously applied on the temporary support by a known application method.

The steps (1) to (4) are general methods for forming images when the photosensitive transfer materials are used and, for example, such a method is disclosed in JP-A No. 5-173320. As a typical image forming method, a method can be used which comprises the steps of superposing the photosensitive resin composition layer formed by the photosensitive transfer material on a surface of a transparent substrate to be equipped at liquid crystal display (LCD) elements; after a temporary support has been peeled off from the substrate, pattern-exposing the photosensitive resin composition layer on a material to be transferred, via a photomask; after the exposure, heating the photosensitive resin composition layer; and dissolving and removing unexposed portions (unnecessary portions) due to the development processing.

As described above, it is preferable that the alkaline soluble thermoplastic resin layer, the intermediate layer, and the like are provided between the substrate and the photosensitive resin layer.

Thermoplastic Resin Layer

The thermoplastic resin layer is easily deformable when stress is applied thereto, and exhibits an effect of increasing adhesiveness of the photosensitive resin layer to the substrate to thereby improve image quality. Further, if a plurality of photosensitive transfer materials are used to form a multi-color image (such as color filters) on the same substrate, when additional colors (in this case, the second color) are transferred, the first color pixels have already been formed on the substrate, and irregularities were formed. Accordingly, for example, when the second color photosensitive resin layer is transferred and formed so as to cover the first color pixels, air gaps are formed due to irregularities, whereby defective transfer tends to be caused. However, use of the thermoplastic resin layer can prevent such a defective transfer.

As the thermoplastic resin to be used, an alkaline soluble thermoplastic resin can be used, and examples thereof include: a saponified substance of a copolymer of ethylene and acrylic ester; a saponified substance of a copolymer of styrene and (metha) acrylic ester; a saponified substance of a copolymer of vinyltluene and (metha) acrylic ester; and a saponified substance of poly (metha) acrylic ester or a copolymer of (metha) acrylic butyl and vinyl acetate.

A thickness of the thermoplastic resin layer is preferably 6 to 100 μm, and more preferably 10 to 50 μm.

Intermediate Layer

From a viewpoint of increasing photopolymerization efficiency due to oxygen blocking, it is preferable to provide an intermediate layer.

As a material to be used for the intermediate layer, it is necessary to use a material which is less deformable when stress is applied thereto, which is able to be applied onto the thermoplastic resin layer, and which is alkaline soluble. Examples of such materials are disclosed in JP-A No. 46-2121 and JP-B No. 56-40824 and include: polyvinyl ether/maleic anhydride polymers, water soluble salts of carboxyalkyl cellulose, water soluble cellulose ethers, water soluble salts of carboxyalkyl starch, polyvinyl alcohol, polyvinylpyrolidone, various polyacrylamides, various water soluble polyamides, water soluble salts of polyacrylic acid, gelatin, ethylene oxide polymers, water soluble salts selected from a group of various starches and the likes; styrene/maleic acid copolymers; maleinate resins, and a combination of two or more of them.

Of these materials, a combination of polyvinyl alcohol and polyvinylpyrolidone is particularly preferable. Polyvinyl alcohol whose saponification rate is 80% or more is preferable, and the content of polyvinylpyrolidone with respect to the total solid components of the intermediate layer is preferably 1 to 75 mass %, more preferably 1 to 60 mass %, and most preferably 10 to 50 mass %.

A thickness of the intermediate layer is preferably 0.1 to 5.0 μm, and more preferably 0.5 to 2.0 μm.

In the same manner as in the case in which the photosensitive resin layer is applied and formed on the substrate, the thermoplastic resin layer and the intermediate layer described above can be formed on the substrate by a known application method after dissolving each of the components for both layers in a solvent that does not adversely affect to neighboring layers to form a coating solution.

Substrate

A substrate is not particularly limited, and can be suitably selected in accordance with the use. However, in preparing color filters, a known glass plate, a soda glass plate having a silicon oxide coating film formed on the surface of the plate, and the like are preferable.

Further, the temporary support that is used when a photosensitive resin composition is provided on a temporary support is not particularly limited, and can be suitably selected in accordance with the use. However, a flexible sheet type support is preferable.

Other Additives

Besides the UV absorbent represented by formula (1), additives such as an oxidation inhibitor, a light stabilizer, and the like can be added to the photosensitive resin composition of the present invention.

As such additives, compounds disclosed in JP-A Nos. 8-225679 and 9-25360 can be used.

EXAMPLES

The following examples further illustrate the present invention in detail, but do not limit the scope thereof. Further, in the following examples, "%" means "mass %", and "part" means "part by mass" unless they are conditioned.

Example 1

<Preparation of Photosensitive Transfer Material>

Compounds consisting of the following composition were mixed to prepare a coating solution for a thermoplastic resin layer.

| [Composition of the coating solution for the thermoplastic resin layer] | |
|---|---|
| a copolymer of benzylmethacrylate/2-ethylhexylacrylate/methylmethacrylate/methacrylic acid (copolymerization ratio: 4.5/11.7/55/28.8, weight average molecular weight: 80000) | 4.5 parts |
| copolymer of stylene/acrylic acid (copolymerization ratio: 60/40, weight average molecular weight: 8000) | 15 parts |
| 2,2-bis[4-(methacryloxypolyethoxy)phenylpropane] | 7 parts |
| F-176PF (a fluorine containing surfactant manufactured by Dainippon Ink & Chemicals, Inc.) | 1.5 parts |
| propylene glycol monomethylether | 28 parts |
| methyl ethyl ketone | 27 parts |

As a temporary support, a polyethylene telephthalate base film (PET base film) whose thickness is 75 μm was prepared, coated with the thermoplastic resin coating solution thus obtained by a spin-coater, and dried in an oven for 5 minutes at the temperature of 120° C. to thereby form a thermoplastic resin layer whose thickness is 15 μm on the PET base film.

Compounds consisting of the following composition were mixed to thereby prepare a coating solution for an intermediate layer. The intermediate layer coating solution was layered and applied onto the thermoplastic resin layer by using the spin-coater. Thereafter, this was dried in an oven for 2 minutes at the temperature of 100° C. to thereby form an intermediate layer whose thickness is 1.6 μm on the thermoplastic resin layer.

| [Composition of the coating solution for the intermediate layer] | |
|---|---|
| polyvinyl alcohol (PVA-205 manufactured by Kuraray Co., Ltd.) | 13 parts |
| polyvinyl pyrolidone (PVP-K30 manufactured by Gokyou Sangyou Co., Ltd.) | 6 parts |
| methanol | 173 parts |
| ion-exchange water | 211 parts |

Compounds consisting of the following composition were mixed to thereby prepare four types of photosensitive resin layer coating solutions for red, green, blue and black (red and blue coating solutions are prepared by using the photosensitive resin composition of the present invention).

| [Composition of a coating solution for a red photosensitive resin layer] | |
|---|---|
| RT-107 (C.I. PR254 dispersion liquid manufactured by Fuji Film Olin Co., Ltd.) | 48.33 parts |
| MMPG-AC (propylene glycol monomethyl ether acetate) | 10.54 parts |
| cyclohexanone | 0.73 parts |
| methyl ethyl ketone | 31.91 parts |
| surfactant (Megafac F-176 manufactured by Dainippon Ink & Chemicals, Inc.) | 0.11 parts |
| phenothiazine | 0.0015 parts |
| copolymer of benzilmethacrylate/methacrylic acid (copolymer ratio: 72:28, a molar weight: 30000) | 0.43 parts |
| dipentaerythritol hexacrylate | 5.11 parts |
| 2-trichloromethyl-5-(p-styrylstyryl-1,3,4-oxadiazol | 0.43 parts |
| the aforementioned exemplified compound No. 1 (UV absorbent; a compound represented by formula (1)) | 2.00 parts |
| [Composition of a coating solution for a green photosensitive resin layer] | |
| GT-2 (C.I. PG36 dispersion solution manufactured by Fuji Film Olin Co., Ltd.) | 15.86 parts |
| YT-123 (C.I. PY138 dispersion solution manufactured by Fuji Film Olin Co., Ltd.) | 11.07 parts |
| MMPG-AC (propylene glycol monomethylether acetate) | 14.67 parts |
| methyl ethyl ketone | 51.60 parts |
| surfactant (Megafac F-176 manufactured by Dainippon Ink & Chemicals, Inc.) | 0.13 parts |
| phenothiazine | 0.004 parts |
| copolymer of benzilmethacrylate/methacrylic acid (copolymer ratio: 72:28, a molar weight: 30000) | 1.21 parts |
| dipentaerythritol hexacrylate | 4.01 parts |
| 2-trichloromethyl-5-(p-styrylstyryl-1,3,4-oxadiazol | 0.193 parts |
| 7-[ [4-(diethylamino)-6-(3-hydroxymethylpyperidino)-s-triadinyl (2)-amino]-3-phenylcoumalin | 1.26 parts |
| [Composition of a coating solution for a blue photosensitive resin layer] | |
| 7075 M (C.I. PB 15:6 dispersion solution manufactured by Mikuni Shikiso Co., Ltd.) | 32.93 parts |
| MMPG-AC (propyleneglycol monomethylether acetate) | 8.45 parts |
| methyl ethyl ketone | 52.50 parts |
| surfactant (Megafac F-176 manufactured by Dainippon Ink & Chemicals, Inc.) | 0.17 parts |
| phenothiazine | 0.022 parts |
| copolymer of benzilmethacrylate/methacrylic acid (copolymer ratio: 72:28, a molar weight: 40000) | 2.185 parts |
| dipentaerythritol hexacrylate | 3.95 parts |
| 2-trichloromethyl-5-(p-styrylstyryl-1,3,4-oxadiazol | 0.202 parts |
| the compound No. 1 (a UV absorbent; a compound represented by formula (1)) | 0.24 parts |
| [Composition of a coating solution for a black photosensitive resin layer] | |
| CFP-FF-775B (C.I. PB 15:6 dispersion solution manufactured by Fuji Film Olin Co., Ltd.) | 6.37 parts |
| CFP-FF-293Y (C.I. PY139 dispersion solution manufactured by Fuji Film Olin Co., Ltd.) | 4.78 parts |
| CFP-FF-802V (C.I. PV23 dispersion solution manufactured by Fuji Film Olin Co., Ltd.) | 5.90 parts |
| CFP-FF-949K (Carbon black dispersion solution manufactured by Fuji Film Olin Co., Ltd.) | 16.88 parts |
| MMPG-AC (propylene glycol monomethylether acetate) | 27.17 parts |
| methyl ethyl ketone | 74.00 parts |
| surfactant (Megafac F-176 manufactured by Dainippon Ink & Chemicals, Inc.) | 0.14 parts |
| hydroquinone monomethylether | 0.0032 parts |
| dipentaerythritol hexacrylate | 6.89 parts |
| bis-[4-[N-[4-(4,6-bistrichloromethyl-s-triazine-2-yl)phenyl]carbamoyl]phenyl]-sebacate | 0.193 parts |

As described above, four PET base films in each of which the thermoplastic resin layer and the intermediate layer are layered in this order were prepared, and each of a red, green, blue or black photosensitive resin layer coating solution was applied onto the intermediate layer of each PET base film by the spin-coater. Thereafter, the PET base films for four colors were dried in an oven for two minutes at the temperature of 100° C. to thereby form a photosensitive resin layer whose thickness is 2.0 μm.

Then, polypropylene films, each having a thickness of 12 μm, were laminated at room temperature to thereby form a protective film on the red, green, blue and black photosensitive resin layers, respectively. A photosensitive transfer material for red pixels (1), a photosensitive transfer material for green pixels (1), a photosensitive transfer material for blue pixels (1), and a photosensitive transfer material for black pixels (1) were prepared on the PET base films. In each of the photosensitive transfer materials, the thermoplastic resin layer, the intermediate layer, the photosensitive resin layer (red, green, blue, or black), and the protective film are layered in this sequential order.

Example 2

A photosensitive transfer material for red pixels (2) and a photosensitive transfer material for blue pixels (2), each comprising the thermoplastic resin layer, the intermediate layer, the photosensitive resin layer (red or blue), and the protective film that are layered in this sequential order, were produced on the PET base films in the same manner as that described in Example 1 except that the exemplified compound No. 2-UV absorbent was used instead of the UV absorbent (the exemplified compound No. 1) that was employed for preparing the coating solutions for the red and blue photosensitive resin layers in Example 1.

Example 3

A photosensitive transfer material for red pixels (3) and a photosensitive transfer material for blue pixels (3), each comprising the thermoplastic resin layer, the intermediate layer, the photosensitive resin layer (red or blue), and the protective film that are layered in this sequential order, were produced on the PET base film in the same manner as that described in Example 1 except that the exemplified compound No. 3-UV absorbent was used instead of the UV absorbent (the exemplified compound No. 1) that was employed for preparing the coating solutions for the red and blue photosensitive resin layers in Example 1.

Example 4

A photosensitive transfer material for red pixels (4) and a photosensitive transfer material for blue pixels (4), each comprising the thermoplastic resin layer, the intermediate layer, the photosensitive resin layer (red or blue), and the protective film layered in this sequential order, were produced on the PET base films in the same manner as that described in Example 1 except that the exemplified compound No. 5-UV absorbent was used instead of the UV absorbent (the exemplified compound No. 1) that was employed for preparing the coating solutions for red and blue photosensitive resin layers in Example 1.

Example 5

A photosensitive transfer material for red pixels (5) and a photosensitive transfer material for blue pixels (5), each comprising the thermoplastic resin layer, the intermediate layer, the photosensitive resin layer (red or blue), and the protective film that are layered in this sequential order, were produced on the PET base films in the same manner as that described in Example 1 except that the exemplified compound No. 7-UV absorbent was used instead of the UV absorbent (the exemplified compound No. 1) that was employed for preparing the coating solutions for the red and blue photosensitive resin layers in Example 1.

Example 6

A photosensitive transfer material for red pixels (6) and a photosensitive transfer material for blue pixels (6), each comprising the thermoplastic resin layer, the intermediate layer, the photosensitive resin layer (red or blue), and the protective film that are layered in this sequential order, were produced on the PET base films in the same manner as that described in Example 1 except that the exemplified compound No. 9-UV absorbent was used instead of the UV absorbent (the exemplified compound No. 1) that was employed for preparing the coating solutions for the red and blue photosensitive resin layers in Example 1.

Example 7

A photosensitive transfer material for red pixels (7) and a photosensitive transfer material for blue pixels (7), each comprising the thermoplastic resin layer, the intermediate layer, the photosensitive resin layer (red or blue), and the protective film that are layered in this sequential order, were produced on the PET base film in the same manner as that described in Example 1 except that the aforementioned exemplified compound No. 10-UV absorbent was used instead of the UV absorbent (the exemplified compound No. 1) which was employed for preparing the coating solutions for red and blue photosensitive resin layers in Example 1.

Comparative Example 1

A photosensitive transfer material for red pixels (8) and a photosensitive transfer material for blue pixels (8), each comprising the thermoplastic resin layer, the intermediate layer, the photosensitive resin layer (red or blue), and the protective film which are layered in this sequential order, were produced on the PET base films in the same manner as that described in Example 1 except that 2,4,6-tris [2,4-bis (methoxycarbonyloxy)phenyl]-1,3,5-triazine (i.e., a UV absorbent precursor) was used instead of the UV absorbent (the exemplified compound No. 1) that was employed for preparing the coating solutions for red and blue photosensitive resin layers in Example 1.

Comparative Example 2

A photosensitive transfer material for red pixels (9) and a photosensitive transfer material for blue pixels (9), each comprising the thermoplastic resin layer, the intermediate layer, the photosensitive resin layer (red or blue), and the protective film which are layered in this sequential order, were produced on the PET base film in the same manner as that described in Example 1 except that a UV absorbent (A) represented by the following formula was used instead of the UV absorbent (the exemplified compound No. 1) which was employed for preparing the coating solutions for red and blue photosensitive resin layers in Example 1:

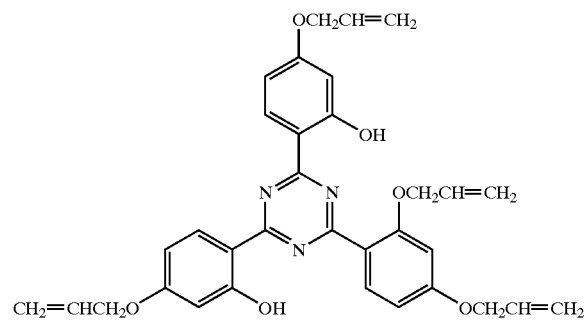

UV absorbent (A)

Comparative Example 3

A photosensitive transfer material for red pixels (10) and a photosensitive transfer material for blue pixels (10), each comprising the thermoplastic resin layer, the intermediate layer, the photosensitive resin layer (red or blue), and the protective film which are layered in this sequential order, were produced on the PET base film in the same manner as that described in Example 1 except that a UV absorbent (B) represented by the following formula was used instead of the UV absorbent (the exemplified compound No. 1) which was employed for preparing the coating solutions for red and blue photosensitive resin layers in Example 1:

UV absorbent (B)

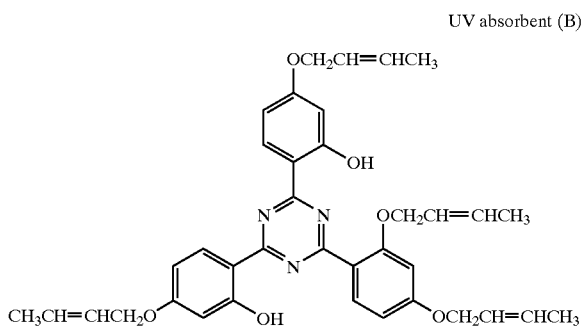

<Evaluation 1>

A thermo-test of the photosensitive transfer materials for red pixels (1) to (7) and (8) to (10) that were obtained as described above was conducted for seven days at the temperature of 30° C.

On the other hand, a glass substrate which was prepared separately was immersed in a silane coupling agent solution (1% diluted solution of KBM-603) for three minutes, washed with water for 10 seconds, dewatered with an air gun, and dried in an oven for five minutes at the temperature of 110° C. to thereby obtain a glass substrate which was subjected to the silane coupling treatment. Ten glass substrates on which the silane coupling treatment was conducted were prepared so as to correspond to the photosensitive transfer materials.

Each protective film was removed from each of the photosensitive transfer material for red pixels (1) to (7) and (8) to (10) for which the termo-test has been completed. The surface of the photosensitive resin layer of each photosensitive transfer material and the silane coupling-treated glass substrate were superimposed so as to come into contact with each other, and adhered to each other by using a laminator (First Laminator 8B-550-80 manufactured by Taisei Laminator Co., ltd.) at a pressure of 2 kg/m$^2$, at a roller temperature of 130° C., and under a conveying condition of 0.2 m/min. Subsequently, the PET base film (temporary support) for each photosensitive transfer material is peeled off from the thermoplastic resin layer at the interface between the temporary support and the thermoplastic resin, and only the temporary support was removed. Consequently, samples (1) to (7) and (8) to (10), each comprising a thermoplastic resin layer, an intermediate layer, and a photosensitive resin layer are layered in this sequential order, were produced on the silane coupling-treated glass substrate.

An aligner MAP-1200L (manufactured by Dainippon Screen Mfg. Co., Ltd.) was used to expose each of the samples (1) to (10) with a super high pressure mercury lamp (500 W/cm) through a photomask for red pixels, for three seconds, at a position of 60 cm from the photosensitive resin layer (irradiation energy: 20 mJ/cm$^2$). After the exposure, the thermoplastic resin layer and the intermediate layer of each sample was dissolved and removed by a predetermined treatment solution (10 times diluted solution of T-PD2 manufactured by Fiji Photo Film Co., Ltd.) to thereby form a red coloring layer.

A microscope was used to check whether or not precipitates were present on the surface of the red coloring layer (photosensitive resin layer) formed in each sample. The results were shown in table 1 below:

TABLE 1

| | Presence of precipitates | | Presence of precipitates |
|---|---|---|---|
| Example 1 | no | Example 6 | no |
| Example 2 | no | Example 7 | no |
| Example 3 | no | Comparative Example 1 | yes |
| Example 4 | no | Comparative Example 2 | yes |
| Example 5 | no | Comparative Example 3 | yes |

As can be seen from the results of table 1, in the photosensitive transfer materials for red pixels (1) to (7) using the composition containing therein the UV absorbent of the present invention, color unevenness was not recognized on the surfaces of red pixels that were formed on the substrate, whereby a red colored layer without image defects was reliably formed. When precipitates of the UV absorbent are present within a layer, if a color filter is prepared by using the layer, irregularities are formed on the surface of the color filter in accordance with the precipitates. Accordingly, cell-gap uniformity deteriorates, color unevenness is caused, and the quality of the color filter thereby deteriorates.

On the other hand, in the photosensitive transfer material for red pixels (8) in which a composition containing therein the UV absorbent of the present invention was not used, a UV absorbent precursor was precipitated on the surface of the coloring layer formed, color unevenness or the like was produced in accordance with the precipitate, and a coloring layer without image defects could not be formed.

In the photosensitive transfer materials (9) and (10) using UV absorbents (A) or (B) which has the same basic skeleton structure as that of the UV absorbent of the present invention but have four alkenyl ether groups, the UV absorbent was precipitated on the surface of the coloring layer formed, color unevenness or the like was produced in accordance with the precipitate, and a coloring layer without image defects could not be formed.

Moreover, when evaluations of the photosensitive transfer materials for blue pixels (1) to (10) were carried out in the same manner as in Evaluation 1, the same results as in the photosensitive transfer materials for red pixels were obtained.

<Preparation of Color Filter and Evaluation Thereof>

Comparative Example 4

A photosensitive transfer material for red pixels (11) and a photosensitive transfer material for blue pixels (11), each comprising the thermoplastic resin layer, the intermediate layer, the photosensitive resin layer (red or blue), and the protective film which are layered in this sequential order, were prepared on the PET base film in the same manner as that described in Example 1 except that a UV absorbent (C) represented by the following formula was used instead of the UV absorbent (the exemplified compound No. 1) that was employed for the preparation of the coating solutions for red and blue photosensitive resin layers in Example 1:

Moreover, the UV absorbent (C) has five ether groups. However, the ether groups cannot be replaced by OH groups even by heating, and are not applicable to the protective groups which can be deprotective due to heating.

UV absorbent (C):

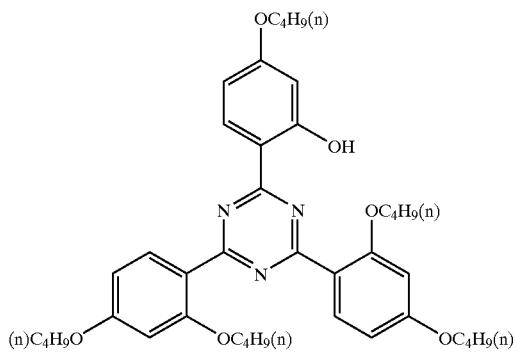

Color filters were prepared by such procedures as described below. Using the photosensitive transfer material for red pixels (1) produced in Example 1, the photosensitive transfer material for green pixels (1), the photosensitive transfer material for blue pixels (1), and the photosensitive transfer material for black pixels (1); and the photosensitive transfer materials for red pixels (2) to (11) and the photosensitive transfer materials for blue pixels (2) to (11) which were prepared in Examples 2 to 7 and Comparative Examples 1 to 4.

First, the photosensitive transfer material for red pixels (1) that was prepared in Example 1 was used, and the same processing as Evaluation 1 was conducted to thereby form a red coloring layer on the silane coupling-treated glass substrate. Here, the thermoplastic resin layer and the intermediate layer were already dissolved and removed, whereby only the red coloring layer consisting of the photosensitive resin layer was formed on the silane coupling-treated glass substrate.

The photosensitive resin layer provided on the substrate in this state was developed by a predetermined treatment solution (5 times diluted solution of T-CD1 manufactured by Fuji Photo Film Co., Ltd.) to thereby dissolve and remove unnecessary portions of the photosensitive resin layer (unexposed region). Further, residual films after the development were removed from the photosensitive resin layer while being brushed with a predetermined treatment solution (10 times diluted solution of T-SD1 manufactured by Fuji Photo Film Co., Ltd.) to thereby form red pixel patterns on the silane coupling-treated glass substrate.

Subsequently, in order to increase the degree of curing of the red pixels, an aligner similar to that in the above-description was used to post-expose the entire surface of the substrate with the super high pressure mercury lamp at the irradiation energy of 20 mJ/cm$^2$ from the rear surface side of the glass surface (i.e., the surface side of the glass substrate on which the red pixel patterns are not disposed), and the substrate having the red pixel patterns is baked in an oven for 20 minutes at the temperature of 220° C.

Then, a protective film was removed from the photosensitive transfer material for green pixels (1). The surface of the photosensitive resin layer of the photosensitive transfer material for green piexles (1) and the surface at the side of the glass substrate having red pixels formed thereon were superimposed and adhered so as to come into contact with each other by using a laminator in the same manner as in the case of forming red pixels patterns. Subsequently, the PET base film of the photosensitive transfer material for green pixels (1) was peeled off from the thermoplastic resin layer at the interface therebetween, and only the temporary support (i.e., the PET base film) was removed from the material at the glass substrate side.

Then, by using the aligner MAP-1200L (manufactured by Dainippon Screen Mfg. Co., Ltd.), the glass substrate, that comprises the photosensitive resin layer (green), the intermediate layer, and the thermoplastic resin layer which are layered sequentially in this order on the red pixels of the substrate, was exposed with the super high pressure mercury lamp (500 W/cm), through a photomask for green pixels, for three seconds at a position of 60 cm from the photosensitive resin layer (irradiation energy: 20 mJ/cm$^2$). After the exposure, the thermoplastic resin layer and the intermediate layer were dissolved and removed by a predetermined treatment solution (10 times diluted solution of T-PD2 manufactured by Fuji Photo Film Co., Ltd.).

Unnecessary portions of the photosensitive resin layer which are unexposed regions were dissolved and removed by using a predetermined treatment solution (5 times diluted solution of T-CD 1 manufactured by Fuji Photo Film Co., Ltd.) and residual films after development were removed while being brushed with a predetermined treatment solution (10 times diluted solution of T-SD 1 manufactured by Fuji Photo Film Co., Ltd.) to thereby form green pixel patterns on the glass substrate having the red pixels formed thereon.

A protective film was removed from the photosensitive transfer material for blue pixels (1). Thereafter, in the same manner as the above-description, the surface of the photosensitive resin layer of the photosensitive transfer material for blue pixels (1) and the surface of the glass substrate at the side at which red and green pixels were formed were adhered to come into contact with each other. Blue pixel patterns are formed on the glass substrate having the red and green pixels formed thereon by removing the temporary support, exposing, dissolving/removing the thermoplastic resin layer and the intermediate layer, developing, removing residual films after the development processing (removing unexposed regions/residual films after the development processing), and baking the pixels formed on the substrate in the same manner as in the case of forming the red and green pixel patterns.

A protective film was removed from the photosensitive transfer material for black pixels (1). Thereafter, the surface of the photosensitive resin layer of the photosensitive transfer material for black pixels (1) and the surface at the side of the glass substrate having the red, green, and blue pixels formed thereon were adhered so as to come into contact with each other, and a temporary support was removed from this material. The aligner MAP-1200L (manufactured by Dainippon Screen Mfg. Co., Ltd.) was used to expose the substrate in which the photosensitive resin layer (black), the intermediate layer, and the thermoplastic resin layer are sequentially layered in this order on the red, green, and blue pixels of the substrate, with the super high pressure mercury lamp (500 W/cm), from the glass substrate at the side at which the pixels and the photosensitive resin layer are not provided (irradiation energy: 70 mJ/cm$^2$). Namely, since the UV absorbent is existent in the red, green, and blue pixel patterns that have already been formed, light to be irradiated does not transmit through the region in which the pixels are formed, whereby the photosensitive transfer material (1) for black pixels is photosensitive only between other pixels. That is, it is photosensitive in the region other than the region in which the red, green, and blue pixel patterns are existent.

A black color matrix is formed in a portion other than the red, green, and blue pixels formed thereon, namely between each of red, green, and blue pixels, of the glass substrate by dissolving/removing the thermoplastic resin layer and the intermediate layer, developing, processing residual films (removing unexposed regions/residual films after development) and baking of the pixels formed on the substrate in the same manner as in a case of forming the red, green, and blue pixel patterns.

In this way, a color filter (1) comprising the red pixels, the green pixels, the blue pixels, and the black matrix was prepared.

The photosensitive transfer materials for red pixels (2) to (11) and the photosensitive transfer materials for green pixels (2) to (11) are used to prepare color filters (2) to (11) in the same manner as the above-description. The number of each photosensitive transfer material corresponds to that of each color filter. Further, in order to prepare the color filter, the photosensitive transfer material for blue pixels (1) and the photosensitive transfer material for black pixels (1) that were prepared in Example 1 were used for the photosensitive transfer materials for blue colors and black colors.

<Evaluation 2>

The color filters (1) to (11) thus formed were evaluated visually by using a microscope whether or not precipitates are present on the surface of each pixels (photosensitive resin layer) and whether or not color evenness is produced.

Consequently, in the color filters (1) to (7) that were prepared by using the composition containing therein the UV absorbent of the present invention, since irregularities due to the generation of precipitates were not recognized on the surface of each of the color filters, it was possible to prepare color filters which do not produce color unevenness and which are excellent in surface smoothness.

Meanwhile, in the color filters (8) to (10) that were prepared without using the composition containing therein the UV absorbent of the present invention, since color unevenness due to precipitation of the UV absorbent was produced on the surface of the color filter, it was impossible to prepare high quality color filters.

Further, in the color filter (11) which was also prepared without using the composition containing therein the UV absorbent of the present invention, since a UV absorbent whose absorption wavelength is long wavelength after heating is not produced when the substrate was baked, if the color filter (11) was exposed in order to prepare black pixels, regions comprising red, green, and blue pixels are exposed to light, whereby black matrix could not be formed thus making it impossible to prepare high quality color filters.

<Evaluation of Dissolving Time of the UV Absorbent in Organic Solvents>

Example 8

Ethyl acetate (10 ml) was added to an eggplant-type flask (100 ml) and stirred at a constant speed at the internal temperature of 25° C. Then, the UV absorbent of the present invention (the exemplified compound No. 1) was measured and added to the flask. When time was measured until powders of the UV absorbent (the exemplified compound No. 1) of the present invention are completely dissolved in the organic solvent, it was 20 seconds.

Example 9

When time was measured until powders of the UV absorbent (the exemplified compound No. 2) of the present invention are completely dissolved in the organic solvent in the same manner as in Example 8 except that the UV absorbent (the exemplified compound No. 2 represented by formula (1)) was used instead of the UV absorbent (the exemplified compound No. 1) that was used in Example 8, it was 12 seconds.

Comparative Example 5

When time was measured until powders of the UV absorbent (C) are completely dissolved in the organic solvent in the same manner as in Example 8 except that the UV absorbent (C) was used instead of the UV absorbent (the exemplified compound No. 1) that was used in Example 8, it was 93 seconds.

Comparative Example 6

When time was measured until powders of a UV absorbent (D) represented by the following formula are completely dissolved in the organic solvent in the same manner as in Example 8 except that the UV absorbent (D) was used instead of the UV absorbent (the exemplified compound No. 1) of the present invention that was used in Example 8, it was 160 seconds.

UV absorbent (D):

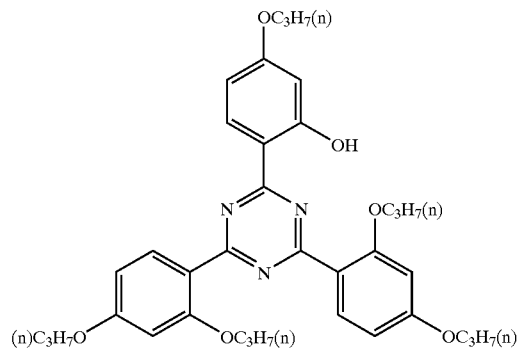

As a result of the evaluation, it was confirmed that the UV absorbent of the present invention has five alkenylether groups, whereby the dissolving time of the UV absorbent in an organic solvent can be reduced. Since the dissolving time of the UV absorbent of the present invention in the organic solvent can be reduced, it was ensured that the UV absorbent of the present invention is excellent in reducing the preparation time of a coating solution containing therein the UV absorbent of the present invention.

As described above, in accordance with the present invention, it is possible to provide a novel UV absorbent which can be used instead of a UV absorbent precursor, whose has a maximum absorption in short wave, and which has an alkenylether group which is a protective group which can be de-protected by heating, which has a low crystallizability, and whose dissolving time in an organic solvent is short. Further, the present invention can provide a method in which the UV absorbent can be prepared in reduced processes and inexpensively.

Moreover, the present invention can provide a composition which contains therein the UV absorbent and which is excellent in storage stability without involving image defects due to crystallization of the UV absorbent even if the composition is stored in an atmosphere of high temperature. In addition, the present invention can provide an image forming method in which images can reliably be formed without image defects such as color unevenness and the like by using a recording material which contains therein the UV absorbent of the present invention and which can form images by heating.

What is claimed is:

1. A UV absorbent represented by the following formula (1):

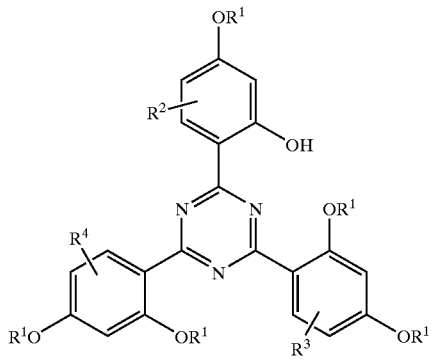

wherein $R^1$ represents an alkenyl group, each $R^1$ represents the same group, and $R^2$, $R^3$ and $R^4$ independently represent a hydrogen atom, an alkyl group, an alkoxy group, or a halogen atom.

2. The UV absorbent of claim 1, wherein the UV absorbent is produced by a reaction between a compound represented by the following formula (2) and an alkenylating agent represented by the following formula (3) in the presence of a base:

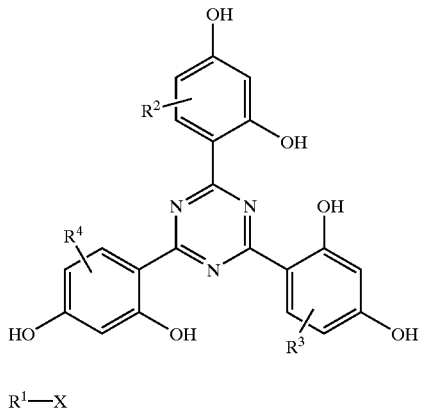

Wherein, in formula (2), $R^2$, $R^3$ and $R^4$ independently represent a hydrogen atom, an alkyl group, an alkoxy group, or a halogen atom, and in formula (3), $R^1$ is an alkenyl group, X represents a halogen atom, $-OSO_2R^5$ or $-OSO_2OR^1$, and $R^5$ represents one of an alkyl group and an aryl group.

3. The UV absorbent of claim 1, wherein the UV absorbent is represented by the following formula (4):

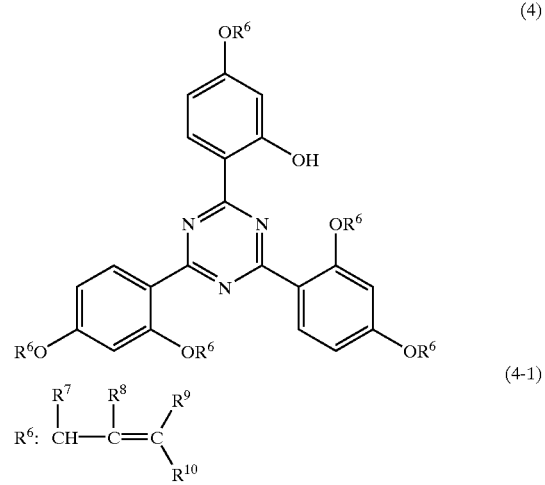

wherein, in formula (4), $R^6$ represents formula (4-1), and $R^7$ to $R^{10}$ in formula (4-1) independently represent one of a halogen atom and an alkyl group.

4. A composition containing therein the UV absorbent of claim 1.

5. The composition of claim 4, further containing therein at least a binder, a polymerizable monomer, and a photopolymerization initiator.

6. The composition of claim 4, further containing therein a colorant.

7. The composition of claim 6, wherein the colorant is a pigment.

8. The UV absorbent of claim 1, wherein $R^1$ in formula (1) is selected from the group consisting of the groups (1) to (12) shown below:

| | |
|---|---|
| $CH_2CH=CH_2$ | (8) |
| $CH_2CH=CHCH_3$ | (2) |
| $CH_2CH=CHC_2H_5$ | (3) |
| $CH_2CH=CHC_3H_7$ | (4) |
| $CH_2CH=CHC_4H_9$ | (4) |
| $CH_2CH=CHC_5H_{11}$ | (6) |
| $CH_2CH=CHC_6H_{13}$ | (7) |
| $CH_2CH=CHC_7H_{15}$ | (8) |

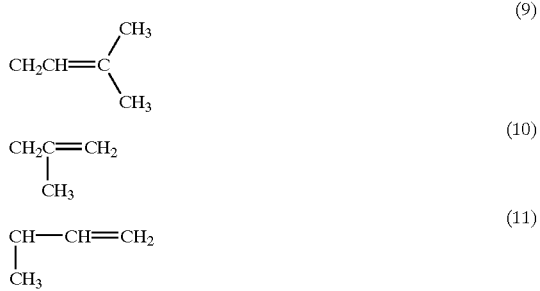

wherein, in formula (1), $R^2$, $R^3$ and $R^4$ independently represent a hydrogen atom, an alkyl group, an alkoxy group, or a halogen atom.

9. The UV absorbent of claim 1, wherein $R^2$, $R^3$ or $R^4$ in formula (1) is a hydrogen atom.

10. The UV absorbent of claim 3, wherein $R^7$ to $R^{10}$ in formula (4) independently represent one of a halogen atom and an alkyl group having 1 to 8 carbon atoms.

11. The UV absorbent of claim 2, wherein X in the alkenylating agent of formula (3) is a halogen atom.

12. The UV absorbent of claim 2, wherein the alkenylating agent of formula (3) is at least one selected from the group consisting of the following alkenylating agents:

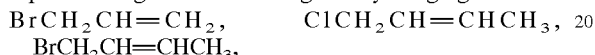
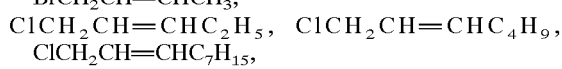
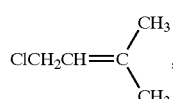
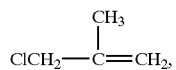
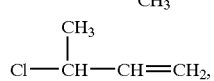
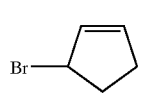

13. The composition of claim 4, wherein the composition comprises a photosensitive resin, and the content of the UV absorbent with respect to the mass of total solid components of the photosensitive resin composition is 0.1 to 30 mass %.

14. The UV absorbent of claim 13, wherein the ratio of transmittance by 365 nm light of a photosensitive resin layer before exposure to a transmittance by 365 nm light of the photosensitive resin layer after heating is 1:0.99 to 1:0.00001.

15. An image forming method comprising the steps of:
a) preparing a composition containing therein a UV absorbent represented by the following formula (1):

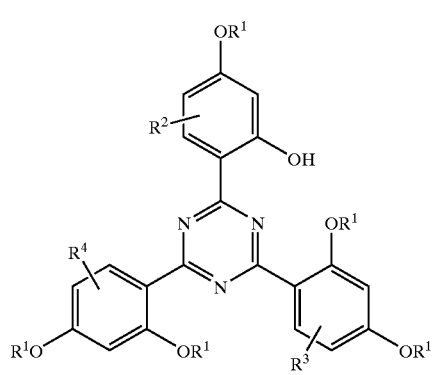

wherein, in formula (1), $R^1$ represents an alkenyl group, each $R^1$ represents the same group, and $R^2$, $R^3$ and $R^4$ independently represent a hydrogen atom, an alkyl group, an alkoxy group, or a halogen atom;

e) applying the composition onto a substrate;

f) exposing the composition on the substrate; removing unnecessary portions of the compositions by development and forming pixels on the substrate; and g) heating the pixels.

16. A method of preparing a UV absorbent represented by the following formula (1) is produced by a reaction between a compound represented by the following formula (2) and an alkenylating agent represented by the following formula (3) in the presence of a base:

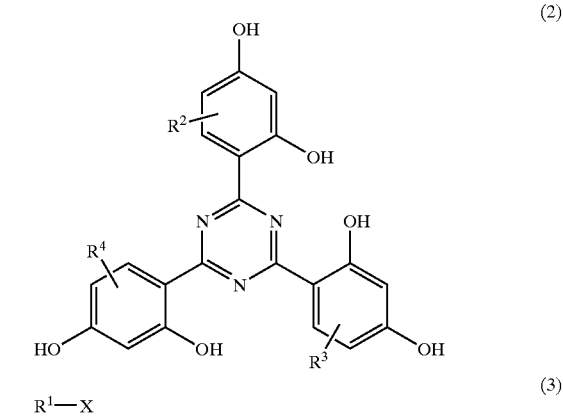

wherein, in formula (1), $R^1$ represents an alkenyl group, each $R^1$ represents the same group, $R^2$, $R^3$ and $R^4$ independently represent a hydrogen atom, an alkyl group, an alkoxy group, or a halogen atom; in formula (2), $R^2$, $R^3$ and $R^4$ independently represent a hydrogen atom, an alkyl group, an alkoxy group, or a halogen atom; and in formula (3), $R^1$ is an alkenyl group, X represents a halogen atom, $-OSO_2R^5$, or $-OSO_2OR^1$, and $R^5$ represents an alkyl group or an aryl group.

17. The method of claim 16, wherein 5 moles or more of the alkenylating agent represented by formula (3) is used with respect to 1 mole of the compound represented by formula (2).

18. The method of claim 16, wherein the base is selected from the group consisting of: inorganic bases comprising sodium carbonate, potassium carbonate, sodium hydrogen carbonate, calcium carbonate, magnesium oxide, cesium carbonate, and sodium acetate and organic bases comprising triethylamine, pyridine, tetramethylammoniumhydroxide, and choline.

19. The method of claim 16, wherein no solvent is used during the reaction.

20. The method of claim 16, wherein a solvent is used during the reaction.

* * * * *